United States Patent [19]
Haugland et al.

[11] Patent Number: 5,208,148
[45] Date of Patent: May 4, 1993

[54] LIPOPHILIC FLUORESCENT GLYCOSIDASE SUBSTRATES

[75] Inventors: Richard P. Haugland; John J. Naleway; Yu-zhong Zhang, all of Eugene, Oreg.

[73] Assignee: Molecular Probes, Inc., Eugene, Oreg.

[21] Appl. No.: 623,600

[22] Filed: Dec. 7, 1990

[51] Int. Cl.⁵ .................. C07H 15/00; C08B 37/02; G01N 33/54; C12Q 1/34
[52] U.S. Cl. .................................. 435/14; 435/19; 435/7.9; 435/7.93; 536/4.1; 536/18.1
[58] Field of Search .............. 435/14, 7.9, 19, 7.93, 435/7.94; 536/4, 18

[56] References Cited
U.S. PATENT DOCUMENTS

| | | | |
|---|---|---|---|
| 4,193,983 | 3/1980 | Ullman et al. | 435/7.9 |
| 4,268,663 | 5/1981 | Skold | 435/7.9 |
| 4,279,992 | 7/1981 | Boguslaski et al. | 435/19 |
| 4,812,409 | 3/1989 | Babb et al. | 435/7 |

OTHER PUBLICATIONS

Chemical Abstracts vol. 115 (11): 109263g (1991).
Chemical Abstracts vol. 114 (5): 38651y (1990).
Chemical Abstracts vol. 105 (21): 186354h (1986).
Chemical Abstracts vol. 97 (16): 133318j (1982).
Chemical Abstracts vol. 84 (19): 133977e (1976).
Chemical Abstracts vol. 116 (13): 122197d (1991).

(List continued on next page.)

*Primary Examiner*—Ronald W. Griffin
*Assistant Examiner*—Louise Leary

[57] ABSTRACT

The claimed invention relates to a substrate for evaluating glycosidic enzymes comprising a fluorescein derivative of the general formula:

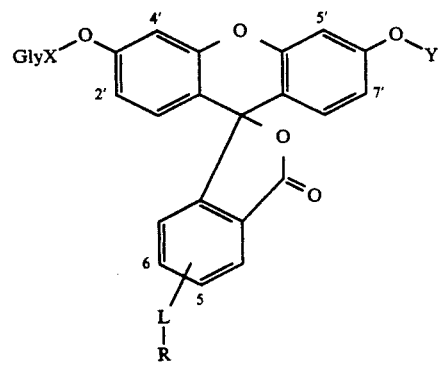

wherein
GlyX is a carbohydrate bonded to fluorescein by a glycosidic linkage;
Y, which may be the same as GlyX or different, is an alkyl ether, an ester, or a glycosidically linked carbohydrate;
R is a lipophilic residue containing from 1 to 21 carbon atoms; and
L links the R residue to fluorescein.

A preferred embodiment of the invention is a non-fluorescent substrate specifically hydrolyzable by a glycosidase inside a cell to yield, after greater than about 2 minutes, a fluorescent detection product excitable at between about 460 nm and 550 nm and with fluorescence observable at an emission wavelength longer than the excitation wavelength, which fluorescent detection product is retained inside a viable cell more than about 2 hours at greater than about 15° C. and which is non-toxic to the cell. A further embodiment of the invention is a method for evaluating a glycosidic enzyme in living plant or animal cells whether the enzyme is present endogenously; present as a result of manipulation of the cell's genome, or added to the cell exogenously, such as by covalently binding the enzyme to a protein to form an enzyme-protein complex that enters the cell.

20 Claims, 6 Drawing Sheets

OTHER PUBLICATIONS

Rotman, et al., "Fluorogenic Substrates for Beta-D-galactosidases and Phosphotases Derived from Fluorescein (3,6-Dihydroxyfluoran) and Its Monomethyl Ether," *Proc. Nat. Acad. Sci.* 50:1 (1963).

Jefferson, "The GUS Reporter Gene System," *Nature* 342:837 (1989).

*Enzyme Nomenclature* pp. 306–326 (Int'l Union Biochem., Academic Press 1984).

Jarvis, et al., "Identification of a DNA segment that is necessary and sufficient for α-specific gene control in *Saccharomyces cerevisiae*: implications for regulation of α-specific and a-specific genes," *Molec. & Cell Biol.* 8:309 (1989).

Legler et al., "Glucosylceramidase from Calf Spleen," *Biol. Chem.* 366:1113 (1989).

Galbraith, "Selection of Somatic Hybrid Cells by Fluorescence-Activated Cell Sorting," *Cell Culture and Somatic Cell Cenetics of Plants* 1:433, ch. 50 (1984).

Nolan, et al., "Fluorescence-activated cell analysis and sorting of viable mammalian cells based on β-D-galactosidase activity after transduction of Escherichia coli lacZ," *Cell Biol.* 85:2603 (1988).

Ikenaka, et al., "Laboratory Methods: Reliable Transient Promoter Assay Using Fluorescein-di--β-D-galactopyranoside Substrate," *DNA & Cell Biol.* 9:279 (1990).

Steinbach, "Characterization of fluorescein isothiocyanate: Synthesis and testing methods for fluorescein isothiocyanate isomers [sic]," *Acta Histochem.* 49:19 (1974).

Emilie et al., "Visualizing interleukin 2 gene expression at the single cell level," *Eur. J. Immunol.* 19:1619 (1989).

Stryer, *Biochemistry* p. 189, W. H. Freeman & Co. Editors (1988).

Jefferson et al., "GUS Fusions: β-Glucuronidase as a sensitive and versatile gene fusion marker in higher plants," *EMBO J.* 6:3901–07 (1987).

Naleway, et al., "New β-Galactosidase Substrates with Improved Cell Retention and Loading Properties in LacZ Positive Cells," *J. Cell Biol.* 111:380a para. 2132 (Nov. 1990).

Petushkova, et al. *Study of Certain Properties of β-Galactocerebrosidase of the Human Chorion Using a Synthetic Fluorogenic Substrate*, translation reprinted from Biokhimya 53, 1539.

Figure 3.a.1
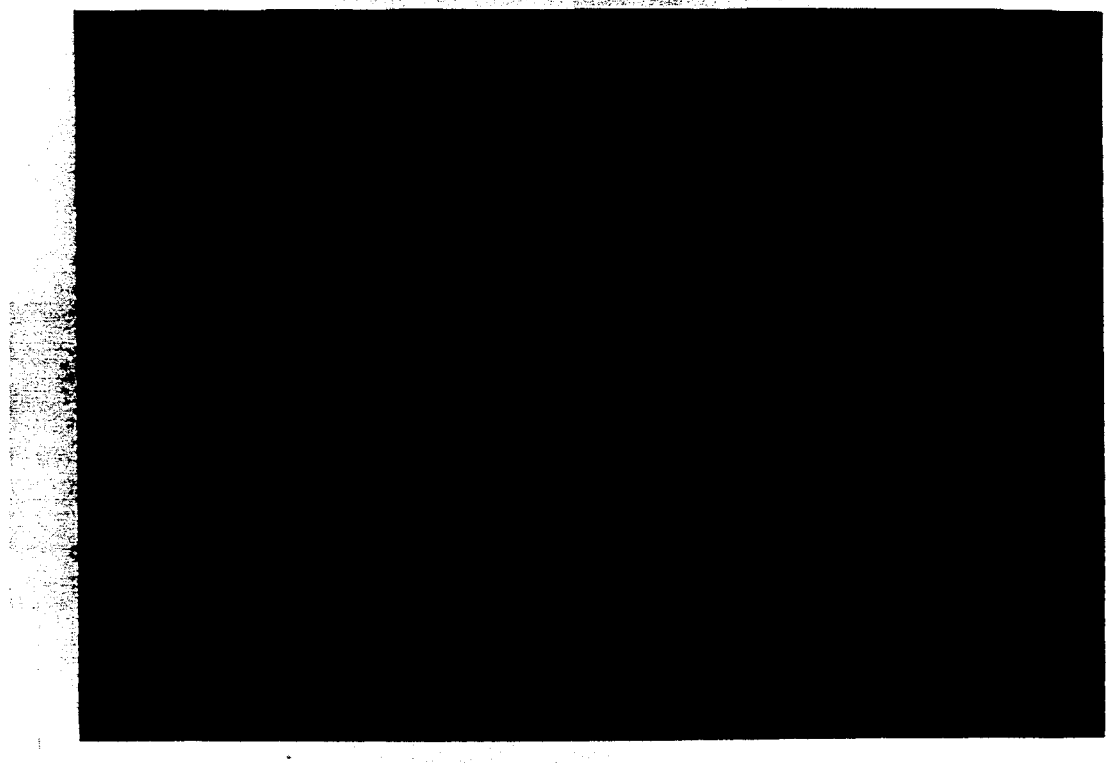
Figure 3.a.2

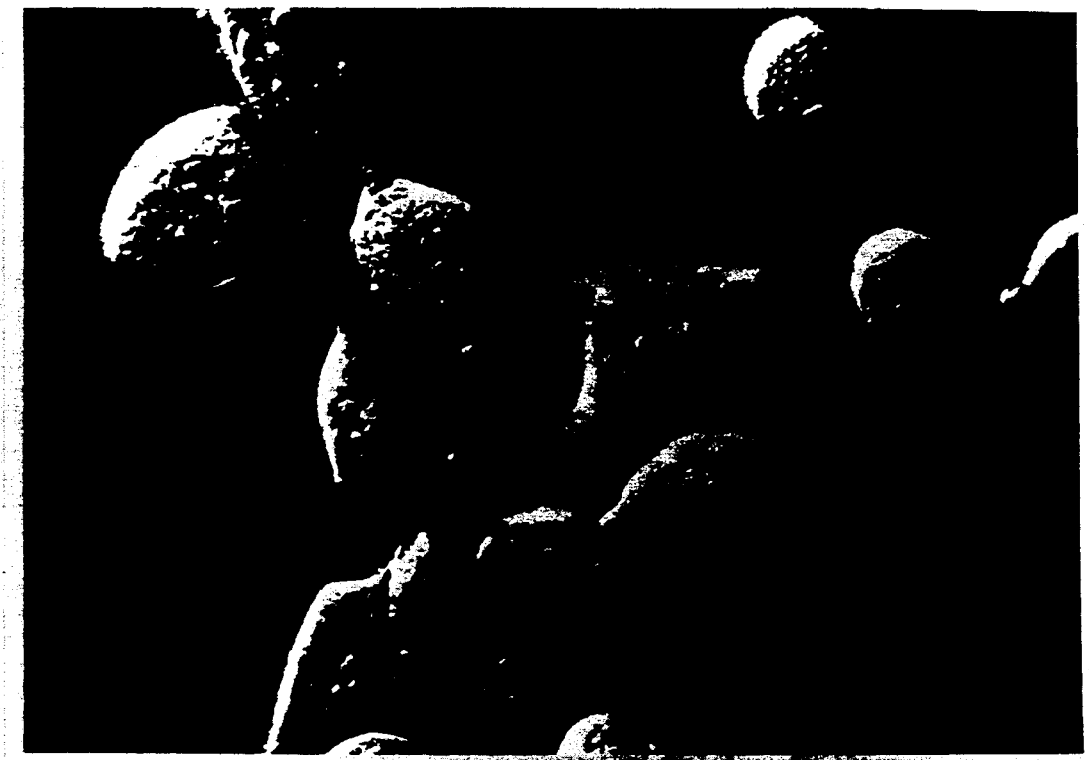
Figure 3.b.1
Figure 3.b.2

Figure 3.c.1
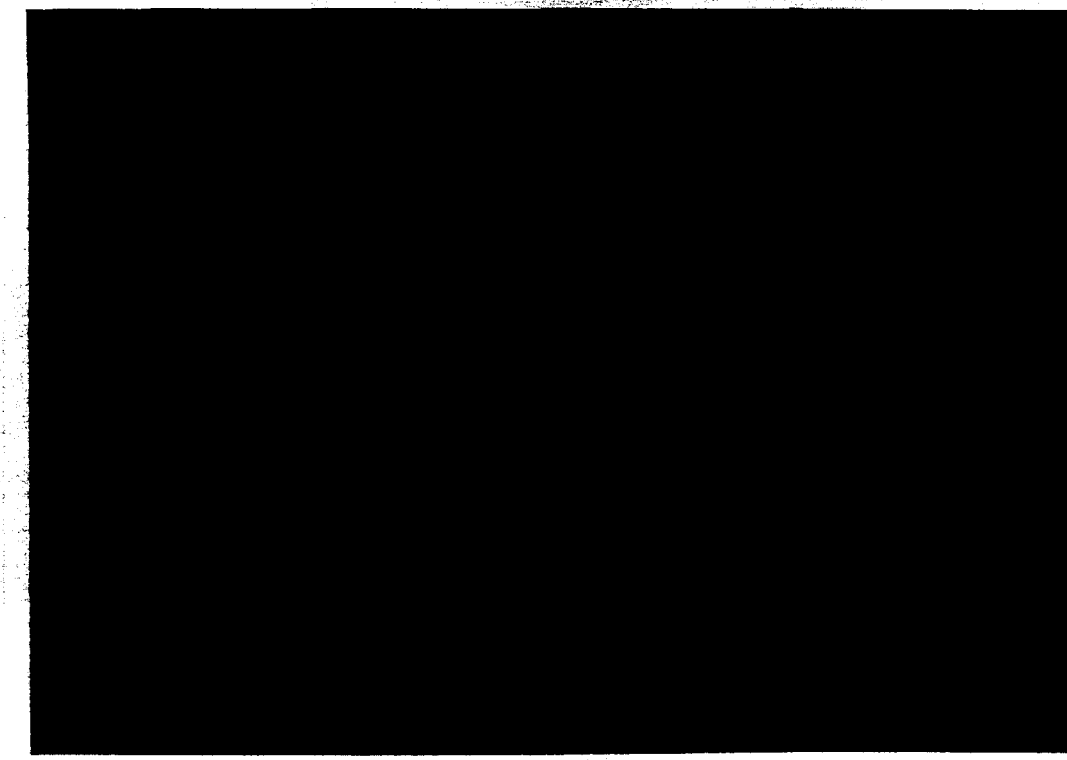
Figure 3.c.2

LIPOPHILIC FLUORESCENT GLYCOSIDASE SUBSTRATES

FIELD OF THE INVENTION

This invention relates to fluorescent substrates used to analyze glycosidic enzyme activity. In particular, the invention relates to an improved fluorescein diglycoside with a lipophilic group, useful in detecting cells producing the enzyme.

BACKGROUND INFORMATION

By studying the chemical reactions that occur inside particular cells, scientists can learn more about those cells. It is difficult to conduct experiments inside cells, however. One technique shown to be useful is to develop a probe to enter the cell, react with a particular substance inside the cell, and signal that the reaction has occurred.

Unfortunately, many tests for the presence of products inside of cells are destructive to the cells being tested, either killing them outright or preventing them from growing or reproducing as normal cells. They may have other disadvantages as well. For example, radioactive substances, while sufficiently sensitive to distinguish cells, ultimately destroy the viability of the cells during measurement and destroy the reproductive capability of the cells. In addition, radioactive reagents are dangerous to handle and require slow and cumbersome experimental techniques and disposal methods, and radioactive measurements can not be done on viable cells. Dyes that are chromogenic rather than fluorescent, e.g., 5-bromo-4-chloroindolyl galactoside (X-gal) and 5-bromo-4-chloro-3-indolyl β-D-glucuronic acid (X-GlcU) are less sensitive and require a large turnover of substrate or multiple reactions to obtain a signal. Furthermore, the hydrolysis product of X-gal (and X-GlcU) is frequently toxic to cells.

In order to study living cells, tests are typically limited to only a portion of a cell population. If the subject cell population is a very small one, however, and some cells are removed for testing, sufficient cells may not be available for further study or use. In order to study or otherwise utilize a small population of cells, as living cells, it is essential to be able to locate and, if possible, separate those cells without destroying them.

Ideally, a probe used to identify and separate a living cell which contains a particular substance or to localize a substance in an organelle of a living cell, has the following characteristics: 1) the probe enters the cell without damaging the cell or preventing its subsequent cloning or reproduction, 2) the probe reacts exclusively with the particular substance inside the cell to form a specific detection product, 3) the detection product produces a signal sufficiently intense to distinguish the cell from other cells that do not contain the substance, and 4) the detection product is sufficiently well retained by the cell to permit analysis and, if desired, sorting of the cell.

Fluorescent enzyme substrates generally make ideal probes. Often, a fluorescent substrate can enter the cell using the cell's own mechanisms. Once inside the cell, a fluorescent substrate usually only reacts with a specific enzyme. Typically, the reaction produces a change in fluorescence which is sufficiently distinctive to distinguish cells or organelles that have the enzyme from cells or organelles that do not.

Use of fluorescent substrates also permits utilization of flow cytometers. Flow cytometers are designed for the rapid and specific sorting of highly fluorescent cells from cells that have low fluorescence. Flow cytometers commonly use an argon laser to excite the fluorescent product inside the cells. Thus, excitation of fluorescence at the principal wavelengths of the argon laser (488 or 514 nm) is a preferred characteristic of a fluorescent substrate. Fluorescent substrates which respond poorly at this wavelength, such as umbelliferone conjugates, have limited applications as a result.

Laser scanning microscopes, including confocal microscopes, also typically utilize the argon laser as the primary excitation source. Scanning of the fluorescence intensity permits a three dimensional representation of the fluorescence distribution to be made.

Quantitative imaging of fluorescence using microscopes and image intensifiers has been used to measure substances such as intracellular calcium ions and superoxide production in living cells. Methods exist for quantitatively measuring changes in fluorescence intensity with time, such as occurs in turnover of fluorescent substrates. Quantitative differences in the fluorescence change that results from hydrolysis of a fluorescent substrate may be the result of either a higher enzyme content or a faster enzyme turnover rate.

Fluorescent substrates, and flow cytometry, can also be used to detect and separate cells which have acquired the ability to produce certain enzymes as a result of a gene fusion. Gene fusions are used to study or work with a particular gene or genetic material by inserting it into a host cell. Typically, the foreign genetic material is inserted into the host cell using a vector (transfection). Alternatively, the foreign genetic material enters the cell through pores created in the membrane, e.g. electroporation, or is microinjected into the host cell. Cells which have successfully incorporated the foreign genetic material are "transformed".

One way to determine whether transformation has occurred is to test for the presence of a protein or product resulting from the inserted genetic material. Depending on the nature of the foreign genetic material inserted into the host cell and the desired genetic characteristics of the transformed cell, however, testing for successful transformation can be expensive and time-consuming.

Glycosidic enzymes are commonly used to differentiate cells, including transformed cells. For example, β-galactosidase is a bacterial enzyme commonly found in *Escherichia coli* (*E. coli*). The enzyme is coded by the *E. coli* lacZ gene. The presence of β-galactosidase activity in a transformed cell can be used to indicate the presence of the foreign lacZ gene. The lacZ gene, in turn, is used as a genetic marker to indicate that additional foreign genetic material, including the lacZ gene, has been incorporated into a host cell otherwise lacking in β-galactosidase. The enzyme β-glucuronidase, coded by the GUS gene in *E. coli*, is primarily used to detect transformation in plant cells and tissues, where this activity is normally lacking (Jefferson, *The GUS Reporter Gene System*, NATURE 342, 837 (1989)), but it is also useful in detecting transformations in mammalian cells.

Not all glycosidic enzymes are useful as marker enzymes, some glycosidic enzymes, such as β-glycosidase, are intrinsically present in many cells. Their activity, however, may be characteristic of the cell type, of an organelle of the cell, or of the metabolic state of the cell.

Some common glycosidic enzymes and representative carbohydrates cleaved by such enzymes are listed in Table 1. This listing is not meant to limit or define the extent of all glycosidic enzymes.

TABLE 1

SELECTED GLYCOSIDIC ENZYMES
(from ENZYME NOMENCLATUE, 1984
(Int'l Union Biochem., Acedemic Press, 1984) 306–26)

| E.C. NO. | GLYCOSIDASE | CARBOHYDRATE-GROUP SELECTIVITY |
| --- | --- | --- |
| 3.2.1.4 | Cellulase | β-Cellobiose |
| 3.2.1.18 | Sialidase | N- or O-Acetyl Neuraminic Acid |
| 3.2.1.20 | α-Glucosidase | α-D-Glucose |
| 3.2.1.21 | β-Glucosidase | β-D-Glucose |
| 3.2.1.22 | α-Galactosidase | α-D-Galactose |
| 3.2.1.23 | β-Galactosidase | β-D-Galactose |
| 3.2.1.24 | α-Mannosidase | α-D-Mannose |
| 3.2.1.25 | β-Mannosidase | β-D-Mannose |
| 3.2.1.26 | β-Fructofuranosidase | β-D-Fructose |
| 3.2.1.30 | N-Acetyl-β-glucosaminidase | β-D-N-Acetyl-Glucosamine |
| 3.2.1.31 | β-Glucuronidase | β-D-Glucuronic Acid |
| 3.2.1.38 | β-D-Fucosidase | β-D-Fucose |
| 3.2.1.40 | α-L-Rhamnosidase | α-L-Rhamnose |
| 3.2.1.43 | β-L-Rhamnosidase | β-L-Rhamnose |
| 3.2.1.48 | Sucrose α-glucosidase | α-D-Glucose |
| 3.2.1.49 | α-N-Acetylgalactosaminidase | α-D-N-Acetyl-Galactosamine |
| 3.2.1.50 | α-N-Acetylglucosaminidase | α-D-N-Acetyl-Glucosamine |
| 3.2.1.51 | α-L-Fucosidase | α-L-Fucose |
| 3.2.1.52 | β-N-Acetylhexosaminidase | β-D-N-Acetyl-Glucosamine |
| 3.2.1.53 | β-N-Acetylgalactosaminidase | β-D-N-Acetyl-Galactosamine |
| 3.2.1.55 | α-L-Arabinofuranosidase | α-L-Arabinose |
| 3.2.1.76 | L-Iduronidase | α-L-Iduronic Acid |
| 3.2.1.85 | 6-Phospho-β-galactosidase | 6-Phospho-β-D-Galactose |
| 3.2.1.86 | 6-Phospho-β-glucosidase | 6-Phospho-β-D-Glucose |
| 3.2.1.88 | β-L-Arabinosidase | β-L-Arabinose |

When the presence of an enzyme is used to indicate gene fusion, the marker included with the foreign genetic material provides a relatively inexpensive means of detecting successful transformation. Cells which have successfully incorporated the marker gene are called "marker" positive (e.g. lacZ+ or GUS+). Using the marker gene to show successful transformation, however, requires detecting the activity of a very small number of enzyme molecules, usually in the cytosol of the lacZ+ or GUS+ cell. The activity must be detected in a way which does not inhibit further use, replication or study of the living transformed cell. Activity of the marker enzyme is most often used to monitor: 1) promotor and/or repressor effectiveness; 2) the crucial sequence of promotor gene after a sequential or selective deletions on it; 3) the level of the induction of the operon so that to evaluate the effectiveness of potential inducer(s); and 4) any possible gene expression regulation at pro- and/or post-transcription or translation level. Such monitoring is done by the methods generally known in the art, such described by Jarvis, Hagen, & Sprague, *Identification of a DNA segment that is necessary and sufficient for α-specific gene control in Saccharomyces cerevisiae: implications for regulation of α-specific and a-specific genes*, MOLEC. & CELL BIOL. 8,309 (1988).

Several substrates derived from fluorescent dyes have previously been described for measurement of glycosidic activity both in cells and of the purified enzyme. Among the most common fluorescent substrates for detection of galactosidase activity are β-methylumbelliferyl galactoside, resourufin galactoside, fluorescein digalactoside, and Naphthol AS-Bl galactoside. Fluorescent substrates for detection of glucuronidase activity include 4-methylumbelliferyl β-D-glucuronic acid, resorufin β-D-glucuronic acid, 4-trifluoromethylumbelliferyl β-D-glucruonic acid, Naphthol AS-Bl β-D-glucuronide, and fluorescein mono-β-D-glucuronide.

Most glycosidase substrates have been designed to be water soluble to facilitate their use in aqueous solution. This hydrophilic character appears to retard passage of the substrate through the membrane of living cells. Legler & Liedtke, *Glucosylceramidase from Calf Spleen*, BIOL. CHEM., 366, 1113 (1985) describes the use of fluorescent glycosidase substrates 4-heptyl-, -nonyl-, and undecylumbelliferone in assaying glucosylceramidase purified from calf spleen. Legler & Liedtke note a preference of the enzyme for long aliphatic side chains in the aglycon. The longer alkyl chains, however, appear to interfere with fluorescence and solubility in the absence of detergents. Legler & Liedtke do not use fluorescein derivatives and do not discuss the assay of glucosidase inside intact living cells.

Although fluorescent substrates are preferable to other methods, such as radioactivity, they are not entirely problem-free. In addition to the problems of cell leakage and cell entry discussed in greater detail below, some of the disadvantages of these substrates include fluorescence at a wavelength not well suited for flow cytometry (e.g. β-methylumbelliferyl galactoside, 4-trifluoromethylumbelliferyl galactoside, naphthol AS-Bl galactoside), pH sensitivity or pH change necessary to exhibit fluorescence (e.g. β-methylumbelliferyl galactoside), and low sensitivity or limited change in fluorescence in the presence of the enzyme (e.g. naphthol AS-Bl galactoside).

U.S. Pat. No. 4,812,409 to Babb et al. (1989) discloses substrates attached to a blocked phenalenone or benzphenalenone fluorescent moiety, which when cleaved from the substrate by hydrolysis at a pH of 9 or less, releases a fluorescent moiety excitable at a wavelength above about 530 nm with maximum fluorescent emission at a wavelength of at least about 580 nm. The spectral properties of the phenalenone or benzphenalenone substrates make these substrates unsuitable for use with flow cytometers which argon lasers because argon lasers excite only at wavelengths of 488 nm and 514 nm. There is also no indication in the patent that the substrate is non-toxic to living cells or that the fluorescent product(s) do not leak from cells after enzymatic turnover.

Fluorescent compounds have been used to detect transformed cells. David W. Galbraith, active in research involving fluorescent dyes used with plant cells, identified four dyes used to label plant cell populations prior to gene fusion in *Selection of Somatic Hybrid Cells by Fluorescence-Activated Cell Sorting*, in CELL CULTURE AND SOMATIC CELL GENETICS OF PLANTS 1, 433, ch. 50 (1984). The four dyes, octadecanoyl aminofluorescein (F18), octadecyl rhodamine B (R18), fluorescein isothiocyanate (FITC) and rhodamine isothiocyanate (RITC) were non-toxic to the cells (although FITC and RITC are toxic at high levels) and did not leak from the cells during culturing (p. 434). The fluorescein dye was added to one cell population, the rhodamine dye to the other. After gene fusion, the presence of both dyes was used to detect the heterokaryons. Galbraith noted (p. 442) that the lipophilic F18 and R18 dyes were observed localized in the membranes of cells, whereas FITC and RITC were distributed through the cytoplasm. Neither set of dyes was used to identify specific enzymes associated with the cells.

An article by Nolan, Fiering, Nicolas, & Herzenberg, *Fluorescence-activated cell analysis and sorting of viable mammalian cells based on β-D-galactosidase activity after transduction of Escherichia coli lacZ*, CELL BIOLOGY 85, 2603 (1988) describes the measurement of galactosidase activity in lacZ+ transformed cells using fluorescein di-62-galactopyranoside (FDG). The use of FDG to measure promoter activity is described in another article, Ikenaka, Fujino, Morita, Iwasaki, Miura, Kagawa, Nakahira, & Mikoshiba, *LABORATORY METHODS: Reliable Transient Promoter Assay Using Fluorescein-β-D-galactopyranoside Substrate, DNA & CELL BIOL*. 9,279 (1990). FDG, originally described in Rotman, Zderic & Edelstein, *Fluorogenic Substrates for Beta-D-galactosidases and Phosphatases Derived from Fluorescein (3,6-Dihydroxyfluoran) and Its Monomethyl Ether*, PROC. NAT. ACAD. SCI. 50, 1 (1963), has excellent properties for detection of this enzyme. Its fluorescent hydrolysis product is fluorescein which has a high absorbance (an extinction coefficient of about 75,000 $cm^{-1}M^{-1}$ at 492 nm) and a high quantum yield (about 0.92 at pH 8.0). Moreover, the absorbance maximum of fluorescein (about 495 nm) results in the dye being excited very well by the argon laser. Furthermore, the substrate FDG is totally nonfluorescent, meaning that the activity measurement can be made with a minimal background fluorescence.

Despite the advantages, there are at least two major drawbacks that are recognized in the use of FDG and all other fluorescent substrates for the analysis and selection of transformed cells. First, it is difficult to get the substrate through the outer cell membrane without disrupting the cell. Nolan, et al., using FDG, reduced this problem for cells in suspension by using brief hypo-osmotic or hypotonic shock. Ikenaka, et al. used the same technique. To use hypo-osmotic shock, the cells are placed in a dilute or hypotonic solution causing the membrane to swell. Swelling of the membrane results in permeabilization of the substrate so that it enters the cell. If the cell stays too long in the dilute solution, however, it ruptures. Removal of the cells from the dilute solution must be carefully time to maximize entry of the substrate yet minimize cell loss.

Because of the low permeability of substrates available, such as 4-methyl umbelliferyl glucuronide, the conventional method for checking the GUS activity in plant tissue is conducted with cell extracts. Such destructive assay will certainly cause inaccuracy and set limitations when investigator is looking for a relatively rare events such as the regulation of transcription and/or translation or the transformation with a chimeric gene.

A second and more important drawback of known fluorescent substrates is the problem of cell leakage. For example, following enzymatic hydrolysis of FDG, the resulting product (fluorescein) rapidly leaks out of the cell. See, e.g., (FIG. 3(c) and FIG. 4; see also, Ikenaka, et al.; Nolan, et al. Commonly half of the fluorescein leaks from the cell in about 10 minutes at about 37° C. Other substrates, including all β-methylumbelliferyl and resorufin glycosides yield fluorescent products with even less desirable spectral properties and have been found to leak even faster than fluorescein. Nolan et al., and Ikenaka, et al., working with FDG, were able to suppress the leakage of fluorescein by quickly cooling their cells to 4° C. Cooling the cells, however, also reduces the enzyme turnover rate significantly, and is not desirable when working with whole living organisms. Leakage of the fluorescent product makes enzyme activity quantitation particularly difficult. It also increases the difficulty in differentiating weakly expressing gene positive cells form the background fluorescence of negative cells.

Neither hypo-osmotic shock loading nor sudden cooling well below physiological temperatures is suitable for measuring activity in transformed living cells, tissues or organisms under physiological conditions such as during development and cell division. What is needed is an improved fluorescent substrate that, in addition to yielding a detectable fluorescent product with absorbance and fluorescence near wavelengths of an argon laser, is also freely permeant to the membrane of the living cell, relatively rapidly yielding a specific fluorescent hydrolysis product. The fluorescent product should be retained in the cell where the hydrolysis occurred for a duration sufficient to make desired measurements. In some cases it may be desirable for the fluorescent product to be retained no longer than a specified time period.

The novel class of substrates included in this invention fully meet all of these requirements. The substrates are permeant to cells physiological conditions, they are not toxic to living cells, they are nonfluorescent until specifically hydrolyzed by the glycosidase enzyme, their fluorescent products are readily detected in single cells and even within specific organelles of single cells, the spectral properties of the substrates permit excitation by the argon laser at its principal wavelengths, and substrates can be selected that yield fluorescent products that are very well retained in the original cell with no or minimal leakage or transfer between marker-positive and marker-negative cells, even through cell division. No other fluorescent substrate, for glycosidic enzymes or for similar enzymes, has previously been described that has this combination of desirable properties.

SUMMARY OF THE INVENTION

This invention describes a class of novel fluorescent substrates for measuring the presence and activity of a glycosidic enzyme. The substrates are particularly effective in detecting glycosidic enzyme activity inside a cell. The novel substrates represent a significant improvement over existing substrates for glycosidic enzymes in that the fluorescent enzymatic hydrolysis products are specifically formed and adequately retained inside living cells, and are non-toxic to the cells. Furthermore, the substrates can penetrate the cell membrane under physiological conditions. These characteristics permit analysis, sorting and cloning of the cells and monitoring of cell development in vitro and in vivo. The substrates are derivatives of fluorescein of the general formula:

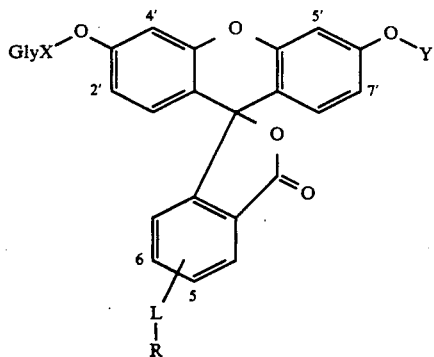

wherein
- GlyX is a carbohydrate bonded to fluorescein by a glycosidic linkage;
- Y, which may be the same as GlyX or different, is an ester, an alkyl ether, or a glycosidically linked carbohydrate;
- R is a lipophilic residue containing from 1 to 22 carbon atoms; and
- L links the R residue to fluorescein.

The sugars of the carbohydrate substituents and their linkage to fluorescein provide the fluorescein-derived substrate with specificity for the particular glycosidic enzymes. Any of the enzymes listed in Table 1, and similar carbohydrate substrates derived form other sugars or modified sugars for which hydrolytic enzymes that hydrolyze the glycosidic linkage, could be detected using fluorescein diglycoside substrates derived from the appropriate sugar(s) specific for the enzyme(s). In further embodiments, the carbohydrates bonded to the fluorescein are different and the substrate is used to detect the presence of either or both enzymes. Hydrolysis of a single glycosidic linkage in a fluorescein diglycoside is sufficient to develop fluorescence, however, greater fluorescence intensity is obtained when both glycosides are hydrolyzed.

Furthermore, the substrate is useful for evaluating a glycosidic enzyme, including the evaluation of a variety of detection, localization, monitoring, and quantitative parameters. The glycosidase enzyme being evaluated inside cells may be present endogenously; present as a result of manipulation of the cell's genome, such as by transformation; or the enzyme may be added to the cell exogenously, for example, by covalently binding the enzyme to a protein to form an enzyme-protein complex that enters the cell. The substrates are also used to test for successful gene fusion. In a preferred embodiment, the substrates are used to monitor whether and to what extent a glycosidic enzyme has been successfully affected by promoters and/or repressors for the enzyme.

The lipophilic residue (R (and L when L is $CH_2$)) appears to provide for the ease of entry into the cells and the enhanced retention within the cells. The preferred lipophilic residue contains an alkyl group of the formula —$(CH_2)_nCH_3$, where n is greater than 1 and less than 22. Those substrates with the longer alkyl chain are better retained by the cell. When it is preferred that the fluorescent product be strongly retained within a cell, preferably the alkyl chain contains 12-18 carbons (n=11-17). When it is preferred that the fluorescent product be only temporarily retained in the cell, the alkyl chain preferably contains 2-8 carbons (n=1-7).

Preferably the lipophilic residue is linked to the single aromatic ring of fluorescein at either the 5 or 6 position. Preferably, the linking group L is alkyl —$CH_2$—, amide —NHCO—, sulfonamide —$NHSO_2$—, carboxyamide —CONH—, carboxylate ester —COO—, urethane —NHCOO—, urea —NHCONH—, or thiourea NHCSNH—.

In a further embodiment of the invention, the xanthene portion of the fluorescein ring structure is substituted at the 2', 4', 5' and/or 7' positions by up to 4 halogen atoms that may be the same or different, including bormine, chlorine, or iodine.

All glycoside substrates are prepared using a modified Koenigs-Knorr methodology in which protected carbonhydrate groups are added to a fluorescein-derived precursor to yield a protected intermediate compound. After isolation of the protected intermediate by column chromatography, the protective groups are removed to yield a hydrophobic fluorescein diglycoside.

DESCRIPTION OF THE DRAWINGS

FIG. 3 is a series of photographs showing fluorescence resulting form use of the novel substrate: (3.a.1 and 3.a.2) $C_{12}FDG$ indicating lacZ cell (d.i.c. pic+-black); (3.b.1 and 3.b.2) $C_{12}$-FDG indicating lacZ+ cell (d.i.c. pic+color); (3.c.1 and 3.c.2) FDG distinguishing lacZ+ cell, but leaking from cell (d.i.c. pic+black). The photographs were taken under a Zeiss Axioplan Microscope equipped with FITC filter set using Fujichrome p1600 color reversal (slide) film. This film was then commercially developed. The black and white photographs were printed from color slides under the following conditions: 1)Internegative using Ilford Panf film, exposed for 1/60 sec. at f11;2) black and white prints on Kodak polycontrast III paper.

DESCRIPTION OF THE PREFERRED EMBODIMENTS

Figure 1:
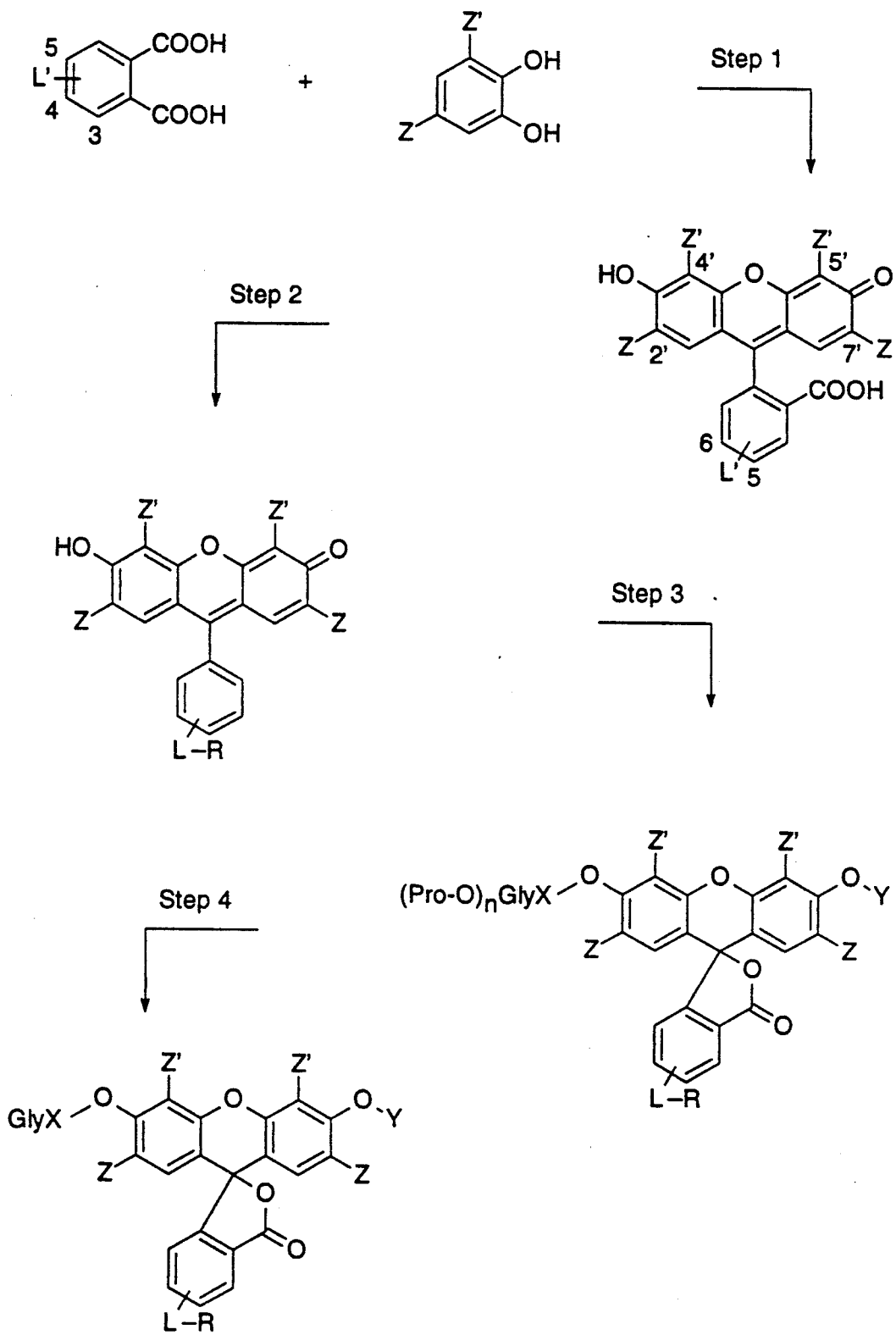
FIG. 1 is a diagram of the formation pathway of the substrate. In step 1, formation of a fluorescein derivative is carried out including either the linking group or its precursor. In step 2, the linking group is modified to attach the lipophilic chain (R). In step 3, the LF is glycosylated, and in step 4, protecting groups are removed to provide the final substrate.
Figure 2:
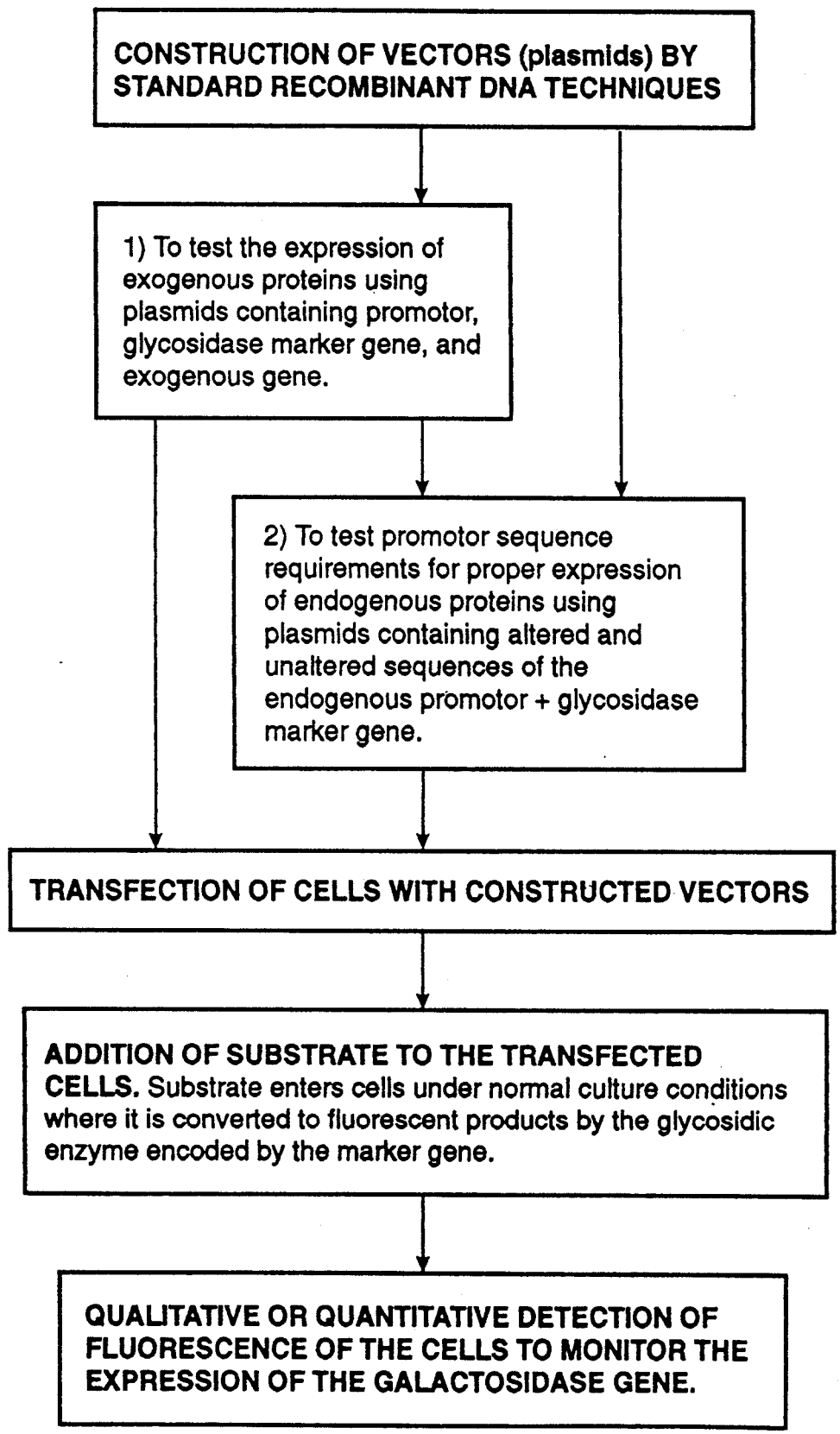
FIG. 2 is a flow chart illustrating the steps required to use the substrate, starting with the construction of the plasmid and ending with the detection of the glycosidase marker gene product.
Figure 4:
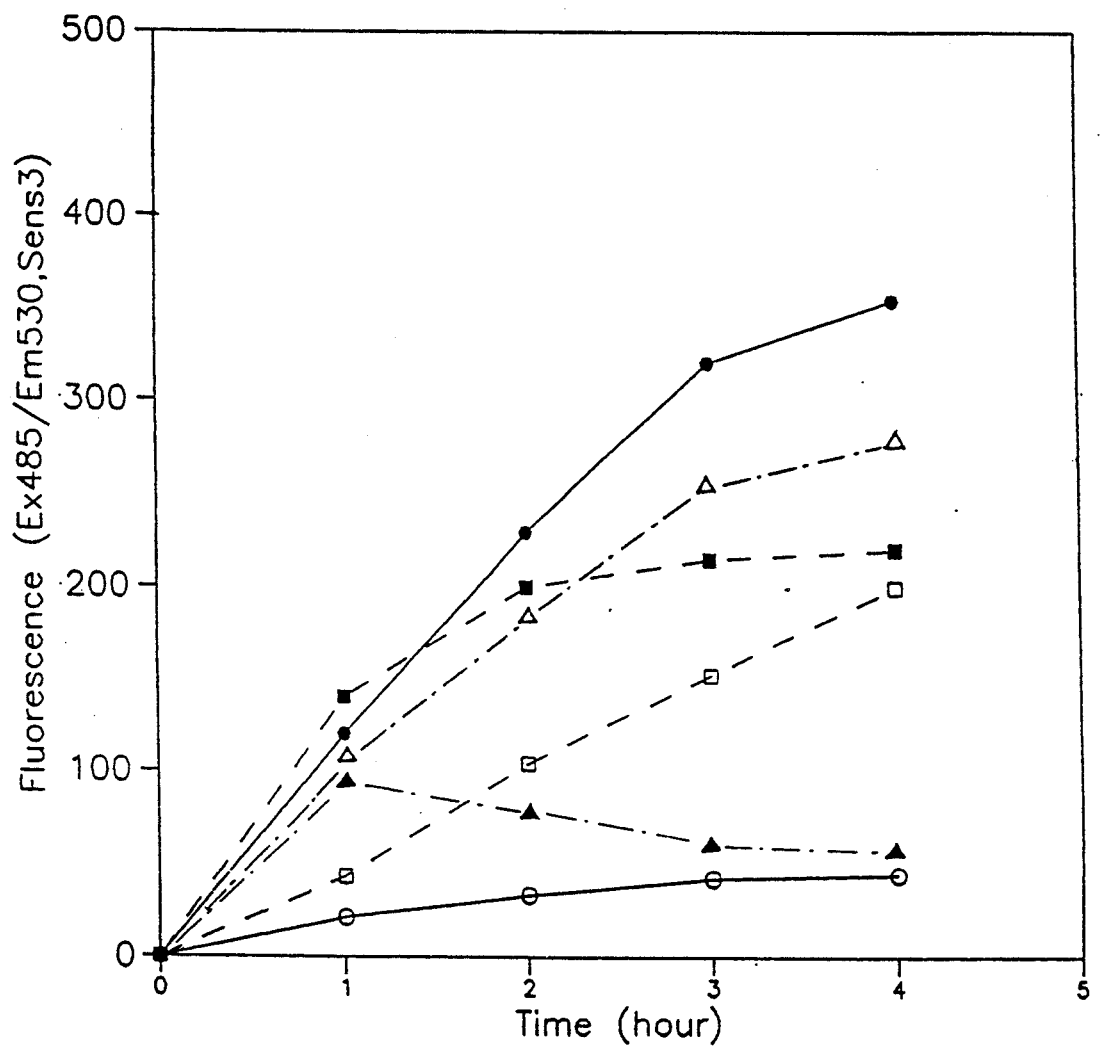
FIG. 4 is graph showing the effect of the fatty chain attached to EDGE on cell fluorescing and lines are defined as follows:
- solid circle: $C_{12}$-FDG: Amount Retained inside of Cells
- open circle: $C_{12}$-FDG: Amount Leaked out in the Medium
- solid square: $C_8$-FDG: Amount Retained inside of Cells
- open square: $C_8$-FDG: Amount Leaked out in the Medium
- solid triangle: FDG: Amount Retained inside of Cells
- Open triangle: FDG Amount Leaked out in the Medium The CRE BAG 2cells (NIH) 3T3 mouse fibroblast, transfected with a retrovirus contained the lacZ gene) were employed in the tests. $C_8$-FDG and $C_{12}$-FDG were loaded into cells through incubation under normal growth conditions while FDG was loaded into cells by hypotonic shock (Nolan et al. 1988) in the beginning.

The subject fluorescent substrates described in this invention are a fluorescein derivative with an attached hydrophobic fatty alkyl or acyl residue. Without wishing to be bound by theory, Applicants believe that the hydrophobic or lipophilic residue facilitates passive diffusion of the substrate through the cell membrane and enhances retention of the fluorescent hydrolysis product, in a form where it is preferentially bound to the cell membranes rather than being free in the cellular cytosol. Binding of the product to a cell membrane considerably enhances retention of the fluorescent product by the cell and considerably reduces transfer of the resulting dye between marker positive and marker negative cells. Increasing the lipophilicity of the fluorescent product by addition of extra methylene groups improves the product retention while decreasing the number of methylene groups accelerates the rate of product clearance. For some applications, it may be preferable that the specific detection product is not retained through cell division (typically, one lifecycle of a cell is from 14–22 hours). This can be accomplished through use of the subject substrates with shorter alkyl residues. The substrate provides the desired permeability, retention, detectability, specificity and lack of toxicity to detect activity of a particular gene in single cells containing the gene.

Specifically the subject substrates contain the 3,6-dihydroxyxanthene structure of fluorescein in which each of the hydroxyl residues is converted to an ether, an ester, or an acetal derived from the sugar(s); and substituted by at least one lipophilic residue containing from 2 to 22 carbon atoms. The substrates have the general formula:

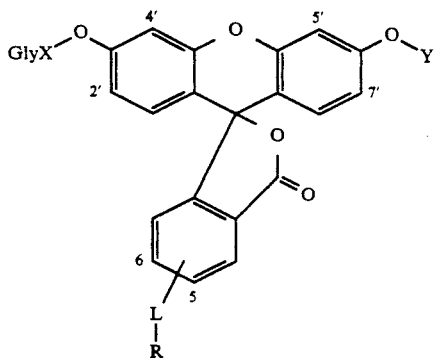

wherein

GlyX is a carbohydrate bonded to fluorescein by a glycosidic linkage;

Y, which may be the same as GlyX or different, is an alkyl ether, an ester, or a glycosidically linked carbohydrate;

R is a lipophilic residue containing from 1 to 21 carbon atoms; and

L links the R residue to fluorescein.

Position numbers, according to standard nomenclature have been added for ease of understanding. Typically, the groups GlyX and Y are the same carbohydrate specific for a particular enzyme.

The lipophilic residue (R), preferably a fatty alkyl or acyl residue, contains from 1 to 21 carbon atoms. Where it is the objective that the fluorescent hydrolysis product be retained less than one lifecycle of a cell, R preferably contains from 1–6 carbon atoms. When longer retention times are the objective, a fluorescein diglycoside derivative containing a lipophilic residue having 11–17 carbon atoms is more preferred because of its overall combination of enzymatic hydrolysis rate, permeability and retention by living cells and spectral properties. Most preferred because of its fluorescence intensity and ease of synthesis is a diglycoside derivative wherein the lipophilic group is attached to fluorescein at either the 5 or 6 position.

The lipophilic group is attached to the fluorophore as an alkyl residue, an amide (including carboxyamides or sulfonamides) derived from an amino derivative of the fluorescein or an ester or amide derived from a carboxylic acid, carbamic acid, or thiocarbamic acid of the fluorescein. Conversion of both hydroxyl groups to glycosides forces the molecule to form a colorless and totally nonfluorescent lactone.

In a further embodiment of the invention, the xanthene portion o the fluorescein ring structure is substituted. For example, halogens can be used to lower the $pK_a$ of the substrate, making it less pH sensitive in the physiological range so that quantitation may be easier. In one embodiment, the ring structure includes halogen substituents at the 2' and 7' positions or at the 4' and 5' positions. Alternatively, halogen substituents are located at the 2', 4', 5', and 7' positions, such as in eosin (2',4',5',7'-tetrabromofluorescein) or erythrosin (2',4',5',7'-tetraiodofluorescein).

All glycoside substrates are prepared using a modified Koenigs-Knorr methodology in which protected carbohydrate groups are added to a lipophilic fluorescein precursor to yield a protected intermediate compound. After isolation of the protected intermediate by column chromatography, the protective groups are removed to yield a lipophilic fluorescein diglycoside.

The starting material for preparation of the lipophilic fluorescein ("LF"), or its respective halogenated derivative. The LF starting material includes at least one lipophilic group containing from 2 to 22 carbon atoms. The preferred LF, because of resultant fluorescence intensity and ease of synthesis, is a lipophilic amide derived from either 5- or 6-aminofluorescein.

In one embodiment of the invention, the xanthene portion of LF is further substituted at the 2', 4',5' and/or 7' positions by up to 4 halogen atoms, that may be the same or different, consisting of bromine, chlorine or iodine. The halogenated LF is used in producing a halogenated lipophilic fluorescein diglycoside.

The LF starting material, including halogenated LF, provides the lipophilic group present in the final product. The lipophilic group is attached to the fluorescein derivative as an alkyl residue, an amide derived from an amino derivative of the fluorescein or an ester or amide derived from a carboxylic acid or thiocarbamic acid of the fluorescein. Non-halogenated LF stock compounds such as fatty acylated amino fluorescein (FAAF) and fatty amide carboxyfluorescein (FACF) are available from Molecular Probes, Eugene, Oreg. or may be synthesized by reaction of 5-aminofluorescein (available from Sigma Chemical Co., St. Louis, Mo.) with an appropriate acyl chloride.

Halogenated LF is prepared by a fluorescein synthesis, such as described in Steinbach, *Characterization of fluorescein isothiocyanate: Synthesis and testing methods for fluorescein isothiocyante isomers* [sic], ACTA HISTOCHEM. 49, 19 (1974) (incorporated by reference), modified to include the use of a halogenated resorcinol. The resorcinol is halogenated at positions calculated to result in the appropriately halogenated fluorescein. The halogenated resorcinol is combined with a phthalic acid substituted at the 4 or 5 position. A substituent at the 4 or 5 position of phthalic acid provides the linking group for attachment of the lipophilic residue in the final substrate. For the amide, urea, and sulfonamide linking groups, the substituent at the 4 position is a nitro function which, after formation of the fluorescein is reduced to an amino function; for the carboxyamide linking group, the substituent at the 4 or 5 position is a carboxy group; and for the alkyl linkage, the substituent is the alkyl group.

A halogenated resorcinol and an appropriately substituted phthalic acid derivative are typically reacted by heated in a 2:1 ratio as a melt, after which the isolated crude fluorescein derivative is typically purified by acetylation, crystalization, and deacetylation. For fluorescein derivatives containing a 5' nitro function, reduction to the corresponding amino derivative is typically performed using sodium sulfide/sodium hydrogen sulfide.

For preparation of a corresponding LF, a halogenated aminofluorescein is typically acylated by reaction with an appropriate acyl chloride, or a halogenated 5' or 6' carboxyfluorescein derivative, as its corresponding N-hydroxysuccinimide form, is typically reacted with an alkyl amine.

Alternately, a halogenated LF substituted at the 4' and 5' positions or at the 2,',4',5' and 7' positions is prepared by direct treatment of a LF with $Cl_2$, $Br_2$ or $I_2$.

From the halogenated or non-halogenated LF starting material, a protected glycoside intermediate is prepared in a multi-step process. Glycosylation using a modified Koenigs-Knorr methodology involves treatment of a LF with a soft acid catalyst, an activated protected carbohydrate (APC) derivative, and a non-nucleophilic base, under anhydrous conditions. Sym-collidine is a preferred non-nucleophilic base and silver carbonate is a representative soft acid catalyst.

The APC will contain one or more sugars with an activating group at the anomeric position of the sugar to be attached to the LF. Typically the APC is a halogenated sugar, where a halogen is the activating group at the anomeric position. Depending on the reaction conditions, the sugar(s) involved, or the anomeric isomer required, other activating groups at the anomeric position of the APC can be used, most commonly trichloroacetimidate, thiophenyl, or acetate.

Using two or more equivalents of an APC, a diglycoside intermediate is formed. Alternately, alkylation or esterification of the remaining hydroxyl group of a monoglycosylated LF will result in the production of a non-fluorescent monoglycoside, monoether or ester intermediate.

After isolation of the protected glycoside intermediate, the protecting groups are removed from the colorless protected diglycoside, alkyl monoglycoside, or the like, using processes appropriate to the protecting group(s) present. For example, catalytic sodium methoxide is used for removal of acetylated alcohols, aqueous lithium hydroxide for methyl esters, etc. Final purification and crystallization yields the non-fluorescent glycoside substrate.

Modifications of the above procedures will be obvious to a chemist skilled in the art of organic chemistry.

To detect the presence of a glycosidic enzyme or enzymes in a substance, a substrate is selected that is specific for those enzyme(s) to be detected. The sugars of the carbohydrate substituents and their linkage to fluorescein provide the substrate with specificity for the particular glycosidic enzymes. The substrate comprising the sugar(s) specific for the enzyme(s) appropriately linked to the fluorescein derivative is combined with the substance being evaluated.

To detect the presence of the glycosidic enzyme in living cells, the substrate is added to the standard culture medium of the cells being evaluated. If the cells being evaluated have been subjected to transformation or other disruptive procedures, the cells should be allowed to stabilize before adding the fluorescent substrate. Typically 12-24 hours rest is sufficient for the cells to stabilize. For adherent cells, growing them on several cover glasses inside a Petri dish will enable cell samples to be taken out at any designated times during the incubation and examined.

For ease of addition to the culture medium, the substrate is dissolved in solution to make a labeling reagent. Preferably the substrate is dissolved in a polar, aprotic organic solvent sufficiently dilute not to disrupt cell membrane structure when the labeling reagent is added to the culture medium. A 10 mM solution of substrate in 20% DMSO yields an effective stock solution of the labeling reagent that remains stable for at least a month if kept sealed in a brown bottle and stored at 4° C.

The labeling reagent is added to culture medium of the cells being evaluated so that the cells incubate further in a labeling culture medium. Some plant cells may only be penetrable as protoplasts after alteration or removal of the cell wall. The labeling reagent is added to the culture medium in an amount sufficient to yield a concentration of about 50 to about 250 $\mu$M of substrate, preferably about 100 to about 200 $\mu$M of substrate, in the labeling culture medium. A sterilized labeling reagent is preferred so that the substrate will be taken up by cells in a normal physiological condition during their growth. Usually the labelling reagent is first added to fresh culture medium to form a fresh labeling culture medium. The fresh labeling culture medium is then filter-sterilized by passing through a low protein-binding, sterilizing filter, such as a 0.20 $\mu$m pore size ACRODISC TM filter. Spent culture medium is removed and sterilized fresh labeling medium is added to culturing cells.

The cells are incubated in the labeling culture for sufficient time for the substrate to enter the cells and to react with the enzyme to yield a fluorescent detection product. Commonly this time is about 1-10 hours. A sample of the cells is observed under a microscope equipped with a filter for visualizing fluorescence. Preferably, the sample of cells is exposed to a radiation source at a wavelength of between about 460 nm and about 550 nm. Washing the cell sample with normal culture medium before examination will reduce background fluorescence from broken cells or decomposed substrate.

The fluorescent detection product is only observed inside cells producing the specific glycosidic enzyme. The substrates can be used to detect activity of the enzyme in any medium, cell-free or not, that contains the enzyme. The glycosidase enzyme being evaluated inside cells may be present endogenously, or present as a result of manipulation of the cell's genome, such as by transformation. In one embodiment of the invention, the presence of the fluorescent detection product is used to indicate the successful insertion of foreign genetic material responsible for the production of the enzyme. In another embodiment of the invention, the presence of the fluorescent detection product is used to show that a promoter for the enzyme is present. In such embodiments involving evaluation of genetic information, appropriate cells are selected for incubation with a suitable substrate specific for the enzyme useful to evaluate such genetic information. Appropriate cells are selected or prepared by means generally known in the art. In the case of evaluating the response of an enzyme with respect to an inducible promoter, the appropriate inducer is subsequently added to the incubated cells.

Regulation of gene expression by inducible upstream elements can be evaluated using a suitable reporter gene and a substrate specific for the product of the reporter gene. Cells containing appropriate genetic material useful for the evaluation of such regulation are selected or prepared according to methods known in the art (Emilie, Peuchmaur, Barad, Jouin, Maillot, Couez, Nicolas, Malissen, EUR. J. IMMUNOL. 19, 1619 (1989) incorporated herein by reference). In yeast, genes that are expressed in a cell-type specific manner and genes whose transcription increases in response to peptide mating pheromones are known. Expression levels of such controlled genes can be related to substrate turnover levels by using lacZ as a reporter gene. The general procedure involves fusing the gene of interest adjacent to the reporter gene and using this construct, usually on a replicating plasmid, in transformation of selected cells. After appropriate growth of the selected cells, the cells are assayed for glycosidase activity using the substrates. The level of activity can be analyzed by fluorescence microscopy or video-fluorescence image analysis at the single cell level by methods known in the art, such as described in Jarvis, et al., MOLEC. & CELL BIOL 8, 309 (1988), incorporated herein by reference. Detection of such induction is facilitated by the improved cell retention properties of the lipophilic galactosidase substrates.

For example, yeast promoters are made up of two components: (1) an upstream activation sequence (UAS) that confers the characteristic regulatory pattern of the gene and (2) a TATA sequence. The full length of UAS will drive a high level of transcription of genes encoded downstream. It is possible to examine whether the complete sequence of the UAS gene is important for the regulation of the transcription of downstream elements. Due to the manipulation of the promotor sequence, different levels of expression of the lacZ gene in each recombinant yeast strain will result in varied $\beta$-galatosidase activities in the transformed yeast cells.

Alternatively, the substrate can be used to evaluate an enzyme added to cells exogenously, for example, by an enzyme covalently bound to a protein to form an enzyme-protein conjugate. The cells are incubated in a conjugate-containing medium. The incubated cells are subsequently washed and transferred to a labeling medium containing substrate specific for the enzyme. After incubating the cells in the labeling medium sufficiently long for the substrate to enter the cells, a portion of the cells are evaluated for fluorescence as above. The presence or absence of a fluorescent detection product is used to determine whether or not the conjugate has entered the cells.

Fluoresence intensity inside the cell will continue to increase until all the substrate has reacted with the enzyme. With more permeable cells, or if successful cell transformation results in abundant enzyme production, fluorescence is observed earlier. In experiments conducted to compare FDG with fatty acylated FDG derivatives, the $C_8$FDG and $C_{12}$FDG both entered the cell more quickly than FDG, but $C_8$FDG was quickly hydrolysed and fluorescence was noticed outside cell after 1 hour. However, retention times up to 72 hours were recorded for FDG derivatives with longer acyl chains. This ability to selectively tune the retention of the fluorescent hydrolysis product inside the cells increases the versatility of the substrates.

The invention can be used to sort cells according their glycosidic enzyme activity. As the substrates generate well cell-retained fluorescence products upon the action of glycosidic enzyme inside cells, an easy and convenient selection/collection of gene-transferred cell of interest is excellently available through a fluorescence-activated cell sorting (FACS) technique. In principle, the substrates are loaded into a cell and then split fluorescent products in an extent determined by glycosidic enzyme activity (or amount) inside the cell. It has been demonstrated (e.g. Nolan, et al.) that modern flow cytometers can sort the cells by their fluorescence signal amplitude therein and, in turn, by cell enzyme activity.

For the sorting of a cell being investigated, the cell is loaded with the glycosidase substrate and incubated to get a sufficient fluorescence signal which corresponds to the cell glycosidic enzyme activity being evaluated. The procedure for cell staining under physiological conditions has been described above. To discriminate cells expressing low enzyme activity from cells that express high levels of enzyme activity, it is preferred to limit the period of incubation to the minimum necessary to achieve the desired resolution. The appropriate balance between sufficient and excessive fluorescence development varies with the substrate concentration, the cell type in terms of membrane permeability for both the substrate and the hydrolysis product, and the distribution of enzyme activity in cell organelles. In a mammalian cell that contains a glycosidic enzyme, 30 to 60 minute incubation rather than hours or overnight, is recommended when a substrate concentration of 50 to 100 $\mu$M is used to stain the cell. Other known automated methods of cell sorting may also be used. There is extensive literature published on cell analysis and sorting instrumentation for flow cytometry. Post-sorting cell examination by other techniques such as assay of enzyme activity or cytochemistry may be needed to confirm the sorting results or to confirm the success of the sorting.

The labeling reagent shows no cytotoxicity. Cells incubated with 0.2 mM $C_{12}$FDG in the culture medium showed the same population doubling time as the control. Cells preincubated in the labeled culture medium for 24 hrs. could be subcultured and the cells of the second generation were normal. The cells grown in 0.2 mM $C_{12}$FDG for 10 days had normal morphology and remained viable. In addition, labelling of cells with $C_{12}$FDG, $C_{16}$FDG, or $C_{18}$FDG, in concentration up to 100 mM, exhibited no detectible toxicity effects as described above.

There are two parameters to describe the catalytic reaction of an enzyme on its substrate. The turnover rate $k_2$, i.e. the substrate conversion rate by one unit of enzyme, can be expressed as $\mu$mol/(minute·mg). The Michaelis constant $K_M$ which gives the substrate binding ability to an enzyme (the smaller is $K_M$, the higher is binding ability), can be expressed as $\mu M$. The relevant data for turnover of five lipophilic FDG substrates by β-galactosidase is detailed in Table 2.

TABLE 2

| Turnover Rates for Representative FDG Substrates in Buffer* | | |
|---|---|---|
| | $k_2$ (μmol/min.mg) | $K_M$ (μM) |
| $C_0$FDG | 1.90 | 18.0 |
| $C_{12}$FDG | 0.0537 | 0.316 |
| $C_{16}$FDG | 0.273 | 1.06 |
| $C_{18}$FDG | 8.28 | 20.8 |

*see Example 8

Transfer of dye between cells was tested in a semi-confluent mixture of enzyme expressing (lac+Z+) and non-expressing (lacZ−) cells. Visualization of adjacent (visible morphological contacts formed) fluorescent and non-fluorescent cells indicated that the fluorescent dye did not transfer between cells.

The following examples are included by way of illustration and not by way of limitation.

EXAMPLE 1

PREPARATION OF A SUBSTRATE HAVING A TWELVE CARBON FATTY ACYL CHAIN AT THE 5-POSITION OF FLUORESCEIN DI-β-D-GALACTOPYRANOSIDE

The following compound was prepared:

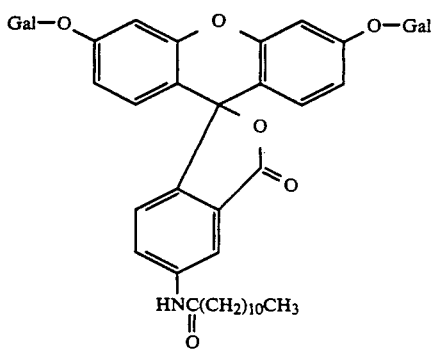

PREPARATION OF
5-DODECANOYLAMINOFLUORESCEIN
DI-β-D-GALACTOPYRANOSIDE,
OCTAACETATE

Under anhydrous conditions, a mixture of 5-(N-dodecanoyl)aminofluorescein (0.976 g, 1.84 mmole), activated 3 Å molecular sieves (0.5 g.), silver carbonate (1.274 g., 4.62 mmole, 2.51 equivalents), and sym-collidine (0.6 mL, 0.55 g, 4.54 mmole, 2.47 equivalents) in anhydrous benzene (10 mL) was allowed to stir in the dark for 1 hour. 2,3,4,6-Tetra-O-acetyl α-D-galactosyl bromide (1.907 g, 4.64 mmole, 2.52 equivalents) was added slowly with stirring over a period of 30 minutes. The above mixture was stirred for 72 hours as described above, after which time it was filtered through a CELITE ™ or diatomaceous earth pad, and the precipitate was washed with chloroform (8×10 mL). The combined filtrates were extracted with 1 M aqueous hydrochloric acid solution (1×100 mL), saturated aqueous sodium bicarbonate solution (2×100 mL), 0.1 M aqueous sodium thiosulfate solution (1×100 mL), and water (1×100 mL), with each aqueous layer being back-extracted with fresh chloroform (5 mL). The combined organic layers were dried over anhydrous sodium sulfate, filtered, evaporated and dried in-vacuo to a bright orange solid (2.51 g., 114%). This crude intermediate was chromatographed on a silicagel G column (100 g.) and eluted by gradient elution using 5% to 20% acetonitrile in chloroform as eluent. Fractions containing the first UV absorbing component to elute from the column were combined and evaporated to a colorless foam (1.31 g., 60%).

PREPARATION OF
5-DODECANOYLAMINOFLUORESCEIN
DI-β-D-GALACTOPYRANOSIDE

To a suspension of 5-dodecanoylaminofluorescein di-β-D-galactopyranoside, octaacetate (1.31 g, 1.20 mmole) in anhydrous methanol (40 mL) was added freshly prepared sodium methoxide (2 mL, 1.87 M solution). The mixture was allowed to stir at room temperature for 2.5 hours, after which time the reaction was neutralized with IRC50 (H+) resin (pH 4), filtered and evaporated to approximately 15 mL total volume. The product was crystallized as an off-white powder by addition of anhydrous diethyl ether (100 mL). The yield of the above product was 681 mg, 75%. An analytical sample of this product was obtained by chromatography on silica gel G using gradient elution with ethyl acetate to 20% methanol in ethyl acetate as eluent. Analysis: calculated for $C_{44}H_{57}O_{17}N$: C, 60.60, H, 6.60. Found: C, 60.13, H, 6.18. M.p=198°-200° C. (d). T.l.c. (7:1:1:1 Ethyl acetate:methanol:water:acetic acid) $R_f$=0.44. $^1$H-n.m.r. ($d_6$-DMSO) δ: 10.4(s,1H,N-H), 8.4(s,1H), 7.8(d,1H), 7.2(d,1H), 7.0(s,2H), 6.7(m,4H), 5.2(s,2H), 4.9(s,2H), 4.9(m, 2H,2×H-1), 4.7(s,2H), 4.5(s,2H), 3.7-3.2 (m,12H), 2.2(t,2H), 1.6(m,2H), 1.2(s, 16H, 0.8(t,3H). HPLC (C-2 column, gradient elution 20-80% $CH_3CN$ in water containing 1% HOAc) k'=4.09.

EXAMPLE 2

PREPARATION OF A PRODUCT HAVING A TWELVE CARBON ALKYL CHAIN BOUND THROUGH AN AMIDE LINKAGE TO 5(6)-Carboxyfluorescein The following compound was prepared:

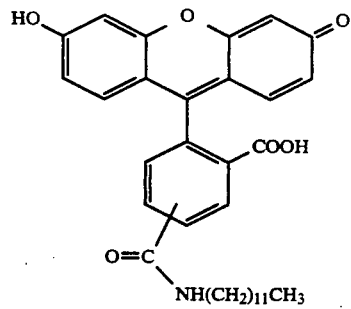

PREPARATION OF
5-(AND-6)-DODECYLAMINOCARBONYL-FLUORESCEIN

To a solution of 5-(and-6)-carboxyfluorescein, N-hydroxysuccinimide ester (502 mg. 1.06 mmole) in anhydrous dimethylformamide (20 mL) was added n-dodecylamine (204 mg, 1.10 mmole, 1.04 equivalent) and triethylamine (2 mL). This mixture was allowed to stir at room temperature for 72 hours. The reaction mixture was poured into ice-water (200 mL) and the product precipitated as a bright orange solid by adjusting the pH of the aqueous solution to pH 4 with 3 M HCl/H$_2$O. The product was filtered and washed with water, dried in air and in-vacuo. Yield of the homogeneous fluorescein derivative was quantitative and the product was used without further purification to prepare diglycosides as described in Example 1. $^1$H-n.m.r. (d$_6$-DMSO) δ:8.7(m,1H), 8.4(s,1H), 8.2(dd,1H), 7.3(d,1H), 6.7(d,2H), 6.5(m,4H), 1.6(m,2H), 1.4–1.2(m,20H), 0.8(t,3H).

EXAMPLE 3

PREPARATION OF A SUBSTRATE HAVING A TWELVE CARBON FATTY ALKYL AMIDE AT THE 5-POSITION OF 2,'7'-Dichlorofluorescein The following compound was prepared:

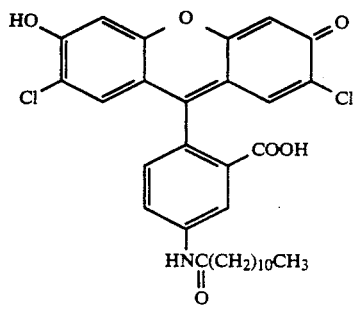

PREPARATION OF 2',7'-DICHLORO-5-NITROFLUORESCEIN DIACETATE

A stainless steel metal cylinder was charged with a finely ground mixture of 4-nitrophthalic acid (100 g. 0.47 moL) and 4-chloroesorcinol (131.5 g, 0.91 moL). This mixture was stirred at 160° C. until the mixture became a brown metal and then for 1 hour, with manual stirring every 3 to 5 minutes. During the next 6 hours the temperature of the wax bath was maintained between 180° C. and 190° C. After cooling to room temperature, the glass-like solid was removed and ground to a fine powder, which was suspended in boiling 6N HCl (2.0 L), filtered and washed with boiling water (3×1.5 L). This solid was dried in-vacuo over KOH at 100° C. for 20 hours to yield 90 g of an orange solid.

This crude intermediate was treated with acetic anhydride (225 mL) at reflux with protection from moisture for two hours. The product was crystallized by slowly cooling to 4° C. A second crop of crystals was obtained after the resulting filtrate was reduced to half its volume and stored at 4° C. Recrystallization form hot benzene (100 mL) gave 6.8 g of product that was shown to be the homogeneous 5-isomer by silica gel t.l.c. (3:2 benzene:ethanol; R$_f$=0.74; 6-isomer R$_f$=0.67), with isomer purity confirmed by $^1$H-n.m.r. spectroscopy.

PREPARATION OF 2',7'-DICHLORO-5-NITROFLUORESCEIN

2',7'-dichloro-5-nitrofluorescein diacetate (6.8 g) was saponified at 50° C. in 5% aqueous saturated sodium hydroxide solution in methanol (300 mL), for 4 hours, after which the reaction mixture was chilled to 0° C. (ice-water bath) and diluted with 1 L of distilled water. Acidification with concentrated HCl (pH 2) gave a light orange precipitate which was collected and washed with distilled water (500 mL) and dried in-vacuo over P$_2$O$_5$ to yield 4.1 g of an orange solid, of suitable purity for synthesis of the amino derivative. T.l.c. (1% acetic acid/15% methanol in chloroform) R$_4$=0.44: (3.2 benzene:ethanol) R$_f$=0.22.

PREPARATION OF 2',7'-DICHLORO-5-AMINOFLUORESCEIN

2',7'-Dichloro-5-nitrofluorescein (4.1 g, 9.1 mmole) was suspended in distilled water (25 mL), under a nitrogen atmosphere and a solution of sodium sulfide nonahydrate (9.5 g, 40 mmole) in water (125 mL) was added. This reaction was stirred at 110° C. (oil bath) until homogeneous, and sodium hydrogen sulfide (4.44 g, 79 mmole) was added. After reflux for 24 hours, the reaction mixture was cooled to 0° C. (ice-water bath) and acidified with acetic acid to give a dark red precipitate. The solid was collected and dissolved in refluxing 6% hydrochloric acid solution (300 mL). This solution was filtered hot to remove elemental sulfur and the filtrate kept at 4° C. overnight to yield a red-orange solid that was collected and washed with distilled water (5 mL). The solid was dried for 24 hours in-vacuo to yield a red-orange solid (1.63 g). T.l.c. (1% acetic acid/15% methanol in chloroform) R$_f$=0.27.

PREPARATION OF 2',7'-DICHLORO-5-DODECANOYLAMINO-FLUORESCEIN

2',7'-dichloro-5-aminofluorescein (1.63 g, 3.1 mmole) was dissolved in dry dimethylformamide (10 mL) containing triethylamine (1.63 mL, 11.7 mmole) and a solution of dodecanoyl chloride (2.60 g, 11.7 mmole) in dry dimethylformamide (5 mL) was added dropwise to the rapidly stirred solution to yield a light red solution plus a precipitate. After stirring for 2.5 hours, the reaction mixture was placed in an oil bath (90° C.) for 45 minutes, cooled to room temperature and stored at −12° C. overnight. The product was isolated by pouring the cold reaction mixture into 15 M sodium hydroxide solution (200 mL). After stirring mechanically 1 hour at room temperature, the basic solution was extracted with hexane (3×200 mL) and acidified with concentrated hydrochloric acid to pH 1, to yield an orange precipitate. The precipitate was dried for 5 hours in-vacuo over P$_2$O$_5$, triturated with diethyl ether (400 mL), and filtered to yield a fine red powder. This powder was crystallized from methanol (2×150 mL) to remove non-dye material. The filtrate was evaporated to dryness and redissolved in 9:1 chloroform:methanol (220 mL) and this solution was extracted with water (10 mL). The organic layer was dried over anhydrous magnesium sulfate, filtered, evaporated under reduced pressure and dried in-vacuo to yield 900 mg of an orange solid. T.l.c.(1% acetic acid/15% methanol in chloroform) R$_f$=0.45. $^1$H-n.m.r. (10% d$_4$-methanol/CDCl$_3$) δ:8.1(d,1H), 8.0(s,1H), 7.1(d,1H), 6.7(s,2H), 6.6(s,2H), 2.4(t,2H), 1.7(m,2H), 1.2(m,16H), 0.8(t,3H).

EXAMPLE 4

PREPARATION OF A SUBSTRATE HAVING TWO GLUCURONIC ACID BLOCKING GROUPS AND A TWELVE CARBON FATTY ACYL CHAIN AT THE 5-POSITION OF FLUORESCEIN

The following compound was prepared:

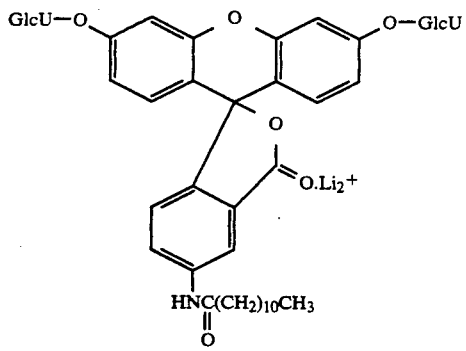

PREPARATION OF 5-DODECANOYLAMINOFLUORESCEIN DI-β-GLUCURONIC ACID HEXAACETATE, DI-METHYL ESTER

Under anhydrous conditions, a mixture of 5-(N-dodecanoyl)aminofluorescein (0.49 g, 0.93 mmole), powdered 4 Å molecular sieve (0.5 g), sym-collidine (306 μL, 2.32 mmoles), silver carbonate (0.643 g, 2.33 mmoles) in anhydrous benzene (20 mL) was allowed to stir in the dark for 1 hour at room temperature. 2,3,4-Tri-O-acetyl α-D-glucopyranosiduronic acid, methyl ester (0.92 g, 2.32 mmoles) was added slowly with stirring over a period of 20 minutes. The above mixture was allowed to stir as described above for 140 hours, after which time it was filtered through a CELITE TM or diatomaceous earth pad, and the precipitate was washed with chloroform until the filtrate was colorless (55 mL). The combined filtrates were extracted with 1 M aqueous hydrochloric acid solution (1×75 mL), saturated aqueous sodium bicarbonate solution (2×75 mL), 0.1 M aqueous sodium thiosulfate solution (1×75 mL), and brine solution (1×75 mL), with each aqueous layer being backextracted with fresh chloroform (5 mL). The combined organic layers were dried over anhydrous sodium sulfate, filtered, evaporated and dried in-vacuo to a bright orange solid (1.26 g, 117%). This crude intermediate was chromatographed on a silicagel G column (100 g) and eluted by gradient elution using 5% to 20% acetonitrile in chloroform as eluent. Fractions containing the first UV absorbing component to elute from the column were combined and evaporated to a colorless powder (0.29 g, 27%).

PREPARATION OF 5-DODECANOYLAMINOFLUORESCEIN DI-β-D-GLUCOPYRANOSIDURONIC ACID, METHYL ESTER

A suspension of 5-dodecanoylaminofluorescein di-β-glucuronic acid, exaacetate, di-methyl ester (280 mg, 0.24 mmole) in anhydrous methanol (30 mL) was cooled to 0° C. in an ice-bath while under an atmosphere of dry nitrogen gas. A solution of freshly prepared sodium methoxide in methanol was added (300 μL, 0.97 M solution) and this mixture allowed to stir at 0° C. for 2.5 hours and at room temperature for 1 hour. After this time, the reaction was neutralized with washed, dry IRC50(H+) resin (pH4), filtered and evaporated to approximately 15 mL total volume. The product was crystallized by addition of anhydrous diethyl ether (100 mL) and storage at −10° C. The white crystalline product formed was isolated on a Nylon 66 membrane filter (0.45 μ pore size), washed with fresh diethyl ether, and dried in-vacuo to an off-white solid (1st crop, 78 mg. 36%).

PREPARATION OF 5-DODECANOYLAMINOFLUORESCEIN DI-β-D-GLUCOPYRANOSIDURONIC ACID, DI-LITHIUM SALT

A solution of 5-dodecanoylaminofluorescein di-β-D-glucuronic acid, di-methyl ester (35 mg, 38.5 μmoles) in water (1 mL) was cooled to 0° C. in an ice-bath, and 0.08 M LiOH solution (1.0 mL, 80 μmoles, 2.08 equivalents) was added. This mixture was allowed to stir at 4° C. for 18 hours, frozen, and lyophilized to a pale yellow foam (30 mg, 88%). M.p.='360° C. T.l.c.(7:1:1:1 ethyl acetate:methanol:water:acetic acid) $R_f$=0.10. $^1$H - n.m.r.($d_6$-DMSO)δ: 10.4(s,1H, N-H), 8.4(s,1H), 7.7(d,1H), 7.2(m,2H), 7.0(d,1H), 6.7(m,4H), 5.2(m,2H,2 x —OH), 5.0(m,6H,2x H-1,4x —OH), 3.2–3.0(m,8H), 2.3(t,2H), 1.6(m,2H), 1.2(s,16H), 0.9(t,3H).

EXAMPLE 5

PREPARATION OF A SUBSTRATE HAVING TWO GLUCOSIDE BLOCKING GROUPS AND A TWELVE CARBON FATTY ACYL CHAIN AT THE 5-POSITION OF FLUORESCEIN

The following compound was prepared:

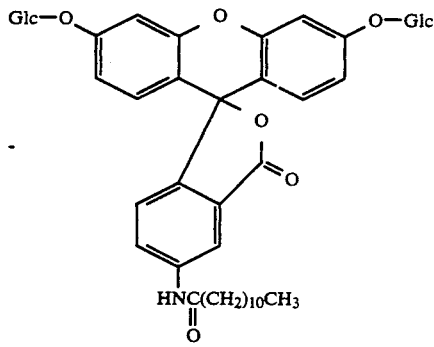

PREPARATION OF 5-DODECANOYLAMINOFLUORESCEIN DI-β-D-GLUCOPYRANOSIDE OCTAACETATE

Under anhydrous conditions, a mixture of 5-(N-dodecanoyl)aminofluorescein (307 mg, 0.58 mmole), powdered, activated 4 Å molecular sieves (0.5 g) and anhydrous benzene was allowed to stir at room temperature for 30 minutes, after which time sym-collidine (195 μL, 1.48 mmole), dry silver carbonate (410 mg, 1.49 mmole) and 1-bromo-2,3,4,6-tetra-O-acetyl β-D-glucopyranoside (612 mg, 1.49 mmole) were added slowly, with stirring. The above mixture was allowed to stir at room temperature, under anhydrous conditions, in the dark for 140 hours. The mixture was filtered through a CELITE TM or diatomaceous earth pad, and the precipitate was washed with chloroform until the filtrate was colorless (35 mL). The combined filtrates were extracted with 1 M aqueous hydrochloric acid solution (1×50 mL), saturated aqueous sodium bicarbonate solution (1×50 mL), 0.1 M sodium thiosulfate solution (1×50 mL) and water (1×50 mL), with each aqueous layer being back-extracted with fresh chloroform (5 mL). The combined organic layers were dried over anhydrous sodium sulfate, filtered, evaporated and dried in-vacuo to an orange oil (860 mg, 124%) which was chromatographed on a column of silicagel G (100 g) using gradient elution from 19:1 to 8:2 chloroform-:acetonitrile as eluent. Fractions containing the first UV absorbing component to elute form the column were combined and evaporated to a colorless foam (208 mg. 30%).

PREPARATION OF 5-DODECANOYLAMINOFLUORESCEIN DI-β-D-GLUCOPYRANOSIDE

A suspension of 5-dodecanoylaminofluorescein di-β-D-glucopyranoside, octaacetate (200 mg, 0.168 mmole) in anhydrous methanol (30 mL) was cooled to 0° C. in an ice-bath while under an atmosphere of dry nitrogen gas. A solution of freshly prepared sodium methoxide in methanol was added (300 μL, 0.97 M solution) and this mixture allowed to stir at 0° C. for 3 hours. The reaction was allowed to warm to room temperature, neutralized with washed, dry IRC50(H+) resin (pH 4), filtered and evaporated to approximately 15 mL at reduced pressure. The product was crystallized by addition of anhydrous diethyl ether (200 mL), filtered on a Nylon 66 membrane filter (0.45 μm pore size), and washed with fresh anhydrous diethyl ether. The white solid obtained was dried in-vacuo, resuspended in water (30 mL) and lyophilized to give 140 mg (98%) of an off-white foam. M.p.=207°-208° C. (d); t.l.c. (7:1:1:1 Ethyl acetate:methanol:water:acetic acid) $R_f$=0.54; $^1$H - n.m.r. ($d_6$-DMSO) δ: 10.3(s,1H,N-H), 8.3(s,1H), 7.8(d,1H), 7.8(d,1H), 7.8(d,1H), 7.2(d,1H), 7.0(m,2H), 6.8(m,4H), 5.4(s,2H), 5.1(s,2H) 5.0(m,2H), 5.0(2H,2x H-1), 4.6(m,2H), 3.6(m,2H), 3.4–3.0(m,12H), 2.4(t,2H), 1.6(m,2H), 1.2(s,16H), 0.8(t,3H). HPLC (C-2 column, gradient elution 20–80% CH$_3$CN in water containing 1% HOAc) k'=4.13.

EXAMPLE 6

LABELING OF LacZ+ CELLS WITH THE FLUOROGENIC SUBSTRATE 5-FATTYACYLAMINOFLUORESCEIN DI-β-GALACTOPYRANOSIDE ($C_{12}$FDG)

CRE BAG 2 (lacZ+) cells were used to test the effectiveness of the substrate in labeling lacZ+ cells. NIH3T3 (lacZ−) cells were used as a control. Both cell lines were obtained from American Type Culture Collection Co., Rockville, Md. The cells were grown in a humidified atmosphere of 5% CO$_2$ in Dulbecco's modified Eagle's medium (DMEM) supplemented with 10% calf serum, 50 μg/ml gentamycin, 300 μg/ml L-glutamine and 10 mM HEPES pH 7.4 (culture medium).

Stock Solution of Labeling Reagent to 1.0 mg of 5-fattyacylaminofluorescein di-β-galactopyranoside substrate ($C_{12}$FDG) was added 0.1193 ml of 20% DMSO to get 10 mM stock solution. Stock solutions were kept sealed in the brown bottle and stored at 4° C.

Labeling Culture Medium

Labelling reagent was added to fresh culture medium in an amount sufficient to make 100 μM $C_{12}$FDG labeling culture medium. Labeling culture medium was filter-sterilized by passing through an ACRODISC™ filter (0.20 μm pore size).

Examination of Cells

Cells were washed with fresh (non-labeling) culture medium before examination. Cells were observed using a microscope equipped with a fluorescein filter. At 60 μM $C_{12}$FDG, after 1 hr. incubation, fluorescence was observed inside CRE BAG 2 cells but not in 3T3 cells. After 6 hrs., the fluorescence intensity in CRE BAG 2 cells reached its highest level.

This labeling reagent showed no cytotoxicity: a. cells incubated in 60 μM $C_{12}$FDG labeling medium showed the same population doubling time as the control; b. cells preincubated in 60 μM $C_{12}$FDG for 24 hrs. were subcultured and the cells of second generation were normal; c. cells grown in 0.2 mM $C_{12}$FDG for 10 days were normal in morphology and appearance.

EXAMPLE 7

SORTING OF LacZ− AND LacZ+ CELLS BY FACS USING GLYCOSIDIC SUBSTRATES

The mixture of cells used for sorting is a mixture of about 50% NIH3T3 (lacZ) and about 50% CRE BAG 2 (lacZ+). The cell source, culturing and substrates labelling procedure are essentially same as EXAMPLE #6: LABELING OF LacZ+ CELLS WITH THE FLUOROGENIC SUBSTRATE. For positive/negative sorting, the substrate is incubated with cells for 5 to 6 hours to achieve a maximum cell fluorescence. For subclone sorting of CRE BAG 2 cells, the substrate incubation should be limited to between 30–60 minutes to permit discrimination of low activity and high activity cells.

Flow Cytometer Instrumentation

Suitable instrumentation for simultaneous analysis and sorting of lacZ+ cells includes a FACS II ™ cell sorter (Becton and Dickinson, Sunnyvale, Calif.). This instrument is typically equipped with an argon ion laser (488 nm, Mountain View, Calif.) and a 70 μM nozzle. Cell autofluorescence is compensated by means of a two-color system. The typical cell velocity is 1000–2000 cells/second. Preferably the cell culture medium without substrate serves as the sheath fluid. The fluorescence of lacZ− cells and lacZ+ cells is typically separated by at least a 10 fold difference in intensities.

Cell Collection and Examination

The sorted cell is collected in a 96 well microtiter plate (Corning, N.Y.). The cell galactosidase activity is examined by means of the permeant fluorogenic substrate resorufin galactoside (Molecular Probes, Inc., Eugene, OR). To 20 μl cell sample in a microtiter well, is added 200 μl of a 0.5 mM resorufin galactoside solution in 0.1 M phosphate buffer containing 1 mM MgCl$_2$ and 0.1% Triton X-100. After 1 hour incubation, the plate is read in a CYTOFLUOR ™ fluorescence plate reader (Millipore, Bedford, Mass.) with excitation at 560 nm, emission at 645 nm, sensitivity=1. A fluorescence reading below 20 can be scored lacZ− cell and a reading higher than 60 can be scored lacZ+. The resorufin galactoside can detect the enzyme activity in a single lacZ+ cell within 1 hour.

EXAMPLE 8

IN VITRO KINETIC ASSAY OF GALACTOSIDASE SUBSTRATES FDG, $C_{12,16,18}FDG$

The substrates have essentially no absorbance at 490 nm while their hydrolysis products from reaction with $\beta$-galactosidase have a strong absorbance at this wavelength. Using the extinction coefficients of the products, the substrate hydrolysis rate can be determined by the absorbance increase at 490 nm (Table 2).

Assay Buffer 13.8 g $NaH_2PO_4.H_2O$, 0.2 g $MgCl_2.6H_2O$ and 7 mL liquid 2-mercaptoethanol are dissolved in 1 liter distilled water and adjusted to pH 7.0 using NaOH.

Substrates Solution

The glycosidase substrates are dissolved at 5 mg/mL in anhydrous DMSO.

Galactosidase Enzyme Solution $\beta$-Galactosidase (Sigma Chemical Co., St. Louis, Mo.) is dissolved at 1 mg/mL in water. This solution is stable for 24 hours at room temperature.

Spectrophotometers

9420 IBM TM UV-Visible.

Assay Procedure and Data Analysis

A series of substrate concentrations between 1 $\mu$M and 1 mM in 2.8 mL of the assay buffer is prepared and pipetted into a cuvette. 0.2 mL of a 1 mg/mL solution of $\beta$-galactosidase in water is added in the cuvette at room temperature to initiate the enzymatic reaction and the absorbance increase at 490 nm is immediately recorded in the spectrophotometer equipped with a chart recorder set at a speed of 10 mm/min. The enzyme reaction rate is calculated using an appropriate product extinction coefficient. Double reciprocal plotting of reaction rate and substrate concentration will yield the turnover rate and Michaelis constant (Stryer, *BIOCHEMISTRY* p. 189 (W. H. Freeman & Co., N.Y. 1988)).

EXAMPLE 9

EVALUATION OF RETENTION LACZ+ CELL FLUORESCENCE ACTIVATION IN VIVO BY $C_{18}FDG$

An experiment was performed to determine the transfer of fluorescent dye to "enzyme deficient" cells, by monitoring the fluorescence emission of adjacent enzyme-positive and -negative cells.

The specimen was contained on a glass coverslip mounted on a small perfusion chamber, attached to a temperature controlled stage and sustained in "near" physiological conditions for 4 hours (buffered physiological pH, room temperature (25° C.)). The chamber was held in a fixed geometry acceptable for optical imaging on a Zeiss Axiovert inverted microscope. Images were collected with a 25/0.8 Zeiss Neofluar water immersion objective; further magnification resulted from a 4× camera relay lens. A "standard" fluorescein epi-fluorescence filter combination was used to monitor the fluorescence. The light levels were imaged with a 2-stage intensified SIT camera, digitized and processed with a Perceptics image processor. The $C_{18}FDG$ substrate was diluted by addition of substrate from 10 milimolar stock in 20% DMSO to DMEM, to give a loading concentrations of 160 micromolar $C_{18}FDG$ in DMEM.

Transfer of dye between cells was tested in a semi-confluent mixture of enzyme expressing (lacZ+) and non-expressing (lacZ−) cells. Results indicated that fluorescent dye did not transfer between cells. This conclusion is based on the visualization of adjacent (visible morphological contacts formed) fluorescent and non-fluorescent cells. The minimum signal level obtained in the imaging was probably affected by a fluorescent background that was present from the first observation of the cells before the substrate entered the cells.

EXAMPLE 10

DETECTION OF GUS GENE EXPRESSION IN TRANSFORMED PLANT CELLS WITH $C_{12}$-FLUORESCEIN DI-GLUCURONIDE

In our cellular assay, the tobacco plant with and without the GUS gene (CaMV35S-GUS, cauliflower mosaic virus 35S promoter with the coding region of GUS) were used. (Ref: Jefferson, R.A., *EMBO J.*, 1987, 6, 3901-3907).

Sections of the stem of both plants were cultured on Murashige and Skoog basal medium with sucrose and agar inside of plant culture dish at 2000 lux, 18 h day, 26° C. The calli were collected from the dishes, cut to small pieces and transferred to liquid medium (in screw cap 50 ml Erlenmeyer flasks) to get cell suspension with shaking (120 rpm) at the culture room. Sterilized 1 mM FA910 solution (in water) was added to the cell suspension to final concentration of 100$\mu$M. After incubating cells in normal condition for 4 h, take 1 ml of suspension, spin down the cells. The cells were resuspended in 100 $\mu$l of fresh culture medium, placed onto glass slide, covered with a cover glass and sealed with wax.

Both the GUS+ and control tobacco cells were examined under a Zeiss microscope equipped with FITC filter set. Photographs were taken of both fluorescent and Nomaski images (Fujichrome P1600D, color reversal film, daylight). Only the GUS gene positive tobacco plant cells were stained with FA910 and show bright yellowish-green fluorescence.

It is to be understood that, while the foregoing invention has been described in detail by way of illustration and example, numerous modifications, substitutions, and alterations are possible without departing from the spirit and scope of the invention as described in the following claims.

What is claimed is:

1. A glycosidase substrate that is a fluorescein derivative of the general formula:

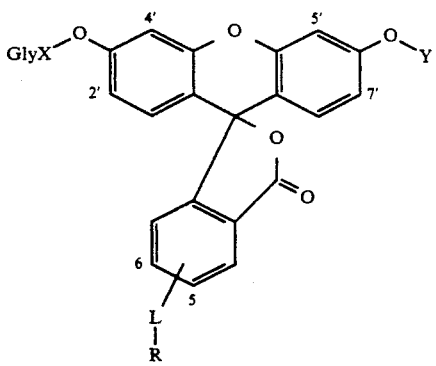

wherein
GlyX is a carbohydrate bonded to fluorescein by a glycosidic linkage;
Y, which may be the same as GlyX or different, is an alkyl ether, an ester, or a glycosidically linked carbohydrate;
R is a lipophilic residue containing from 1 to 21 carbon atoms; and
L links the R residue to fluorescein.

2. A substrate, as claimed in claim 1, wherein both Y and GlyX are carbohydrates bonded to fluorescein by a glycosidic linkage.

3. A substrate, as claimed in claim 2, wherein Y is the same carbohydrate as GlyX.

4. A substrate, as claimed in claim 2, wherein each of the carbohydrates is linked to the fluorescein derivative in a β-glycosidic linkage through an anomeric carbon atoms of said carbohydrate.

5. A substrate, as claimed in claim 1, wherein GlyS is selected from the group consisting of β-D-galactose, β-D-glucose, and β-D-glucuronic acid.

6. A substrate, as claimed in claim 1, wherein the lipophilic residue R comprises an alkyl —(CH$_2$)$_n$CH$_3$, where n is greater than 1 and less than 22.

7. A substrate, as claimed in claim 6, wherein n is greater than 1 and less than 11.

8. A substrate, as claimed in claim 6, wherein n is greater than 9 and less than 18.

9. A substrate, as claimed in claim 1, wherein R is linked to the fluorescein derivative at the 5 or 6 position.

10. A substrate, as claimed in claim 1, wherein said linking group L is alkyl —CH$_2$—, amide —NHCO—, or carboxyamide —COHN—.

11. A substrate, as claimed in claim 1, further comprising substituents attached to a xanthene portion of the fluorescein derivative.

12. A substrate, as claimed in claim 11, wherein said substituents are halogens attached to the xanthene portion at the 2',4',5',7' positions or at the 2',7' positions, or at the 4',5' positions.

13. A substrate, as claimed in claim 1, wherein
both GlyX and Y are β-D-galactose;
R comprises an alkyl —(CH$_2$)$_n$CH$_3$, where n is greater than 10 and less than 18; and L, which is alkyl —CH$_2$—, amide —NHCO—, carboxyamide —CONH—, carboxylate ester —COO—, urethane —NHCOO—, thiourea —NHCSNH—, urea —NHCONH—, or sulfonamide —NHSO$_2$—, links R to the fluorescein derivative at the 5 or 6 position.

14. A substrate, as claimed in claim 13, wherein R is —(CH$_2$)$_{10}$CH$_3$, and L is alkyl —CH$_2$—, amide —NHCO—, or carboxyamide —CONH—.

15. A non-fluorescent substrate that is a lipophilic fluorescein derivative specifically hydrolyzable by a glycosidase inside a cell to yield, after greater than about 2 minutes, a fluorescent detection product excitable at between about 460 nm and 550 nm and with fluorescence observable at an emission wavelength longer than the excitation wavelength, which fluorescent detection product is retained inside a viable cell more than about 2 hours at greater than about 15° C. and which is non-toxic to the cell.

16. A method for evaluating a glycosidic enzyme in a sample comprising the steps of:
a) contacting the sample to be evaluated with a non-fluorescent substrate that is a fluorescein derivative of the general formula

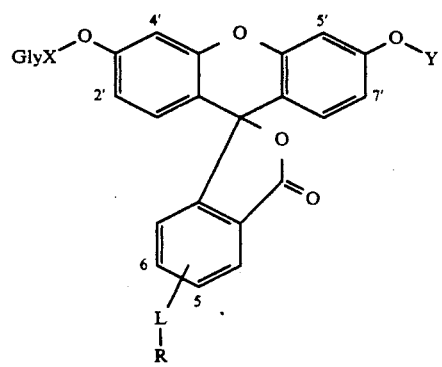

wherein
GlyX is a carbohydrate bonded to the fluorescein derivative by a glycosidic linkage and is specifically hydrolyzable by said enzyme to yield a fluorescent fluorescein analog;
Y, which may be the same as GlyX or different, is an alkyl ether, an ester, or a glycosidically linked carbohydrate;
R is a lipophilic residue containing from 1 to 21 carbon atoms, and
L links the R residue to the fluorescein derivative;
b) removing a first portion of said sample;
c) exciting said first portion of the sample with a radiation source at a wavelength of between about 460 nm and about 550 nm; and
d) observing the first portion in conjunction with means for the detecting fluorescence intensity of the fluorescent analog.

17. A method, as claimed in claim 16, for evaluating a glycosidic enzyme inside living cells, wherein said step of contacting the sample with the substrate comprises incubating said cells in a medium containing said substrate for sufficient time, such that said substrate enters said cells.

18. A method, as claimed in claim 17, for evaluating a glycosidic enzyme inside transformed living cells, wherein said step of removing a first portion from said sample comprises the steps of:
a) removing from the sample, cells containing said fluorescent fluorescein analog;
b) transferring the removed cells to a culture medium containing standard nutrients for growing the removed cells;

c) culturing the removed cells to yield said first portion.

19. A method, as claimed in claim 17, for evaluating a glycosidic enzyme inside transformed living cells containing an inducible promoter, further comprising the steps of:
   a) removing a second portion of said sample;
   b) adding an inducer specific for said promoter to said second portion;
   c) exciting said second potion of the sample with a radiation source at a wavelength of between about 460 nm and about 550 nm; p1 d) observing said second portion in conjunction with means for the detecting fluorescence intensity of the fluorescent analog; and
   e) comparing observation of said second portion with observation of said second portion.

20. A method, as claimed in claim 16, wherein the sample comprises a $\beta$-glycosidase-protein construct.

* * * * *

UNITED STATES PATENT AND TRADEMARK OFFICE
CERTIFICATE OF CORRECTION

PATENT NO. : 5,208,148
DATED : 05/04/93
INVENTOR(S) : R.P. Haugland, J.J. Naleway, Y.-Z. Zhang It is certified that error appears in the above-identified patent and that said Letters Patent is hereby corrected as shown below:

Column 1, above FIELD OF INVENTION, insert --This invention was made with government support under Grant number 38987 awarded by the National Institutes of Health. The government has certain rights in this invention.

Signed and Sealed this

First Day of March, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   : 5,208,148
DATED        : May 4, 1993
INVENTOR(S)  : Haugland, et al.

It is certified that error appears in the above-indentified patent and that said Letters Patent is hereby corrected as shown below:

At col 8, line 12, "bormine" should be --bromine--.

At col 8, line 50, "EDGE" should be --FDG--.

At col 17, line 55, "form" should be --from--.

At col 18, line 7, "$R_4=0.44$" should be --$R_f=0.44$--.

At col 19, lines 1-15, the formula should appear as follows:

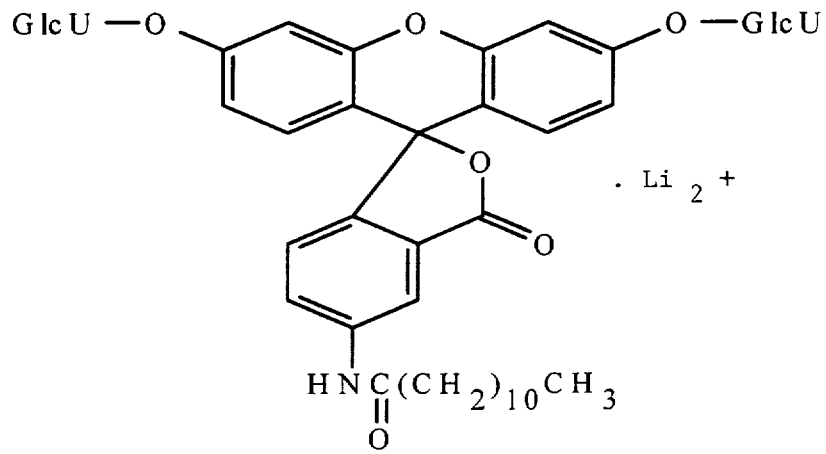

UNITED STATES PATENT AND TRADEMARK OFFICE
CERTIFICATE OF CORRECTION

PATENT NO. : 5,208,148
DATED : May 4, 1993
INVENTOR(S) : Haugland, et al.

It is certified that error appears in the above-indentified patent and that said Letters Patent is hereby corrected as shown below:

At column 19, line 55, insert --D-- before "glucuronic"--.

At col 19, line 55, "exaacetate" should be --hexaacetate--.

At col 22, line 24, "(lacZ)" should be --(lacZ⁻)--.

At col 25, line 35, "GlyS" should be --GlyX--.

At col 28, line 3, "nm; pl d)" should be --nm; d)--.

Signed and Sealed this

Twenty-second Day of October, 1996

Attest:

BRUCE LEHMAN

Attesting Officer                    Commissioner of Patents and Trademarks